US012639807B2

(12) United States Patent (10) Patent No.: US 12,639,807 B2
El-Sallam et al. (45) Date of Patent: May 26, 2026

(54) TRACKING, ANALYSING AND ASSESSMENT OF HUMAN BODY MOVEMENTS USING A SUBJECT-SPECIFIC DIGITAL TWIN MODEL OF THE HUMAN BODY

(71) Applicant: Amar El-Sallam, South Perth (AU)

(72) Inventors: Amar El-Sallam, South Perth (AU); Jacqueline Alderson, North Fremantle (AU); Andrew Lyttle, East Park (AU)

( * ) Notice: Subject to any disclaimer, the term of this patent is extended or adjusted under 35 U.S.C. 154(b) by 330 days.

(21) Appl. No.: 17/899,659

(22) Filed: Aug. 31, 2022

(65) Prior Publication Data

US 2024/0070854 A1     Feb. 29, 2024

Related U.S. Application Data

(60) Provisional application No. 63/226,078, filed on Jul. 27, 2021.

(51) Int. Cl.
*G06T 7/00* (2017.01)
*G16H 10/60* (2018.01)
*G16H 30/20* (2018.01)

(52) U.S. Cl.
CPC ........... *G06T 7/0012* (2013.01); *G16H 10/60* (2018.01); *G16H 30/20* (2018.01); *G06T 2207/20081* (2013.01)

(58) Field of Classification Search
CPC ......... G06T 7/0012; G06T 2207/20081; G06T 2207/10016; G06T 2207/30196; G06T 2207/30221; G06T 7/344; G06T 7/20; G06T 7/285; G16H 10/60; G16H 30/20; G16H 20/30; G16H 50/20; G06V 40/23; A61B 5/11; A61B 5/0022; A61B 5/0024; G06F 2218/08
See application file for complete search history.

(56) References Cited

U.S. PATENT DOCUMENTS

| | | | | |
|---|---|---|---|---|
| 7,274,803 B1 * | 9/2007 | Sharma | ................ | G06V 40/107 |
| | | | | 382/128 |
| 11,042,215 B2 * | 6/2021 | Chen | ...................... | G06F 3/017 |
| 2003/0125099 A1 * | 7/2003 | Basson | ................ | A63F 13/212 |
| | | | | 463/7 |

* cited by examiner

*Primary Examiner* — Akwasi M Sarpong
*Assistant Examiner* — Michael L Burleson

(57) ABSTRACT

The invention relates to systems and methods for the capture, tracking, analysis and assessment of human movements, action or behavior using novel digital quantum twin model of the human. The model is integrated and reinforced by novel representations and novel techniques in computer vision, machine learning, speech processing, sport science, exercise and health. The aim is to achieve optimal analysis and assessment of human motion and other impacting internal and external forces using valid quantum physics-based model of the human combining movements, behaviors, and other health info.

Unlike existing approaches derived from two-or three-dimensional landmarks or just the shape or composition e.g. those extracted from images, videos or sensors, this invention develops an accurate finite element-like quantum representations of human-specific body combining shape features, anatomical structure, internal particles, their intensity, classifications and is constraint by clinical, physical, and biomechanical characteristics of the body and forces affecting each particle.

22 Claims, 13 Drawing Sheets

An overall summary of the invented system leading to the twin quantum human model and the procedure needed for accurate capture, tracking analysis and assessments of movement.

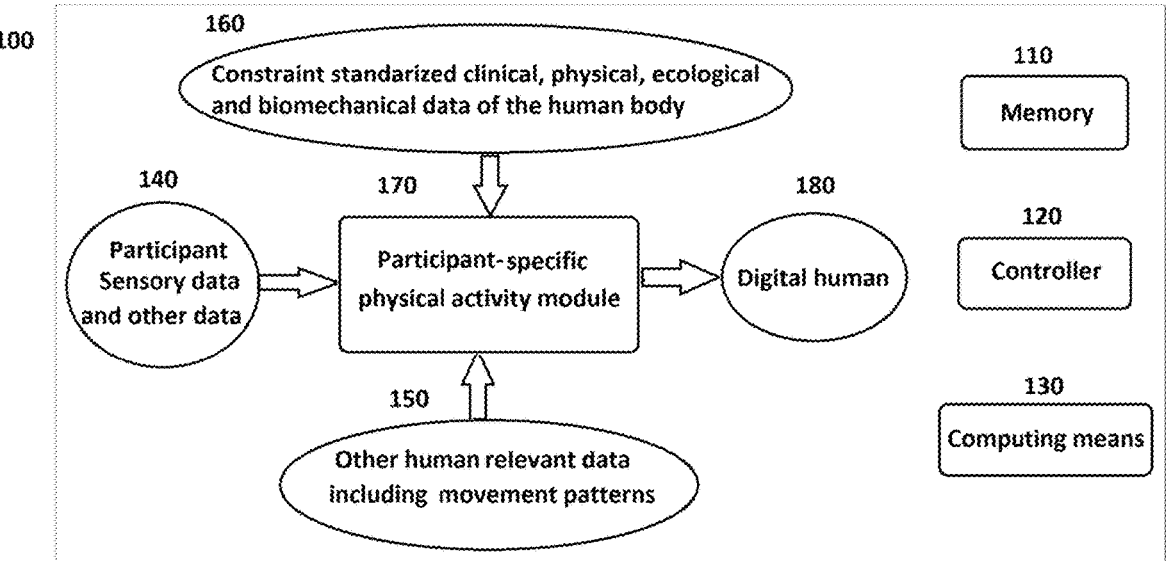
Fig. 1: An overall summary of the invented system leading to the twin quantum human model and the procedure needed for accurate capture, tracking analysis and assessments of movement.

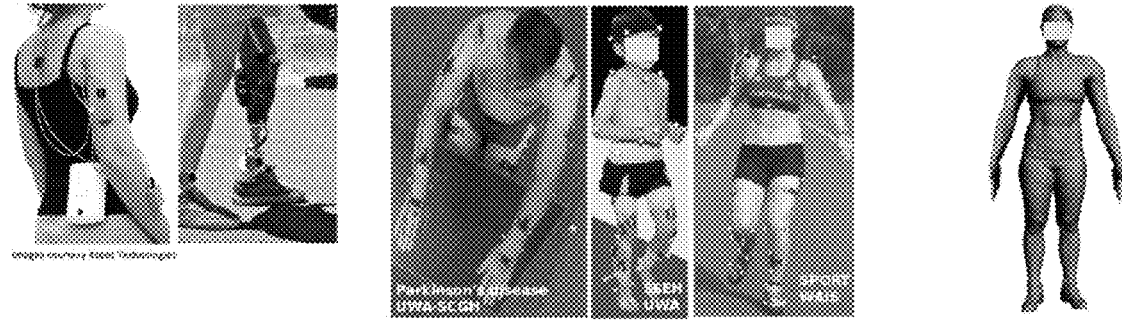

Fig. 2A: Some examples of various human movement data acquired and used in this invention including images, marker and marker-less data, and 3D shapes.

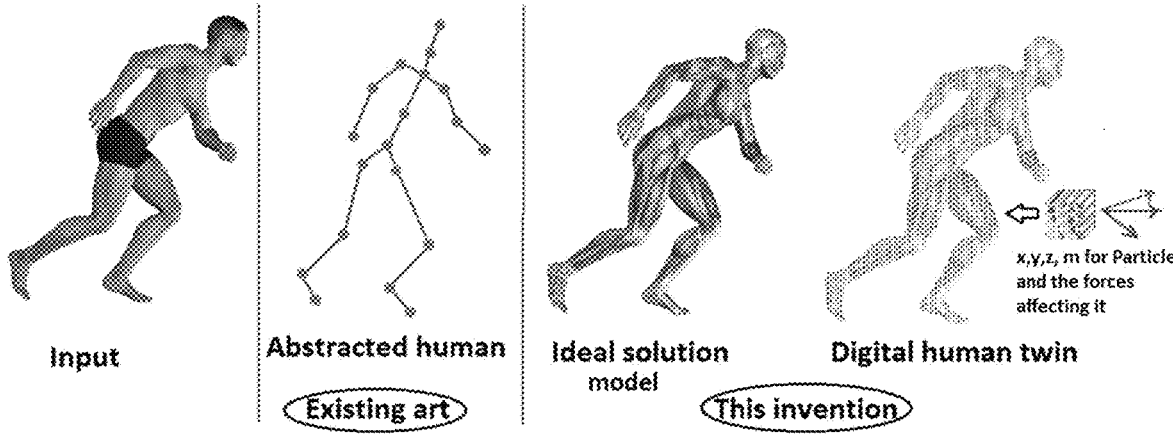

Input          Abstracted human          Ideal solution model          Digital human twin Existing art          This invention x,y,z, m for Particle and the forces affecting it

Fig. 2B: An example clarifying the developed digital quantum human model of a person in a dynamic movement scenario.

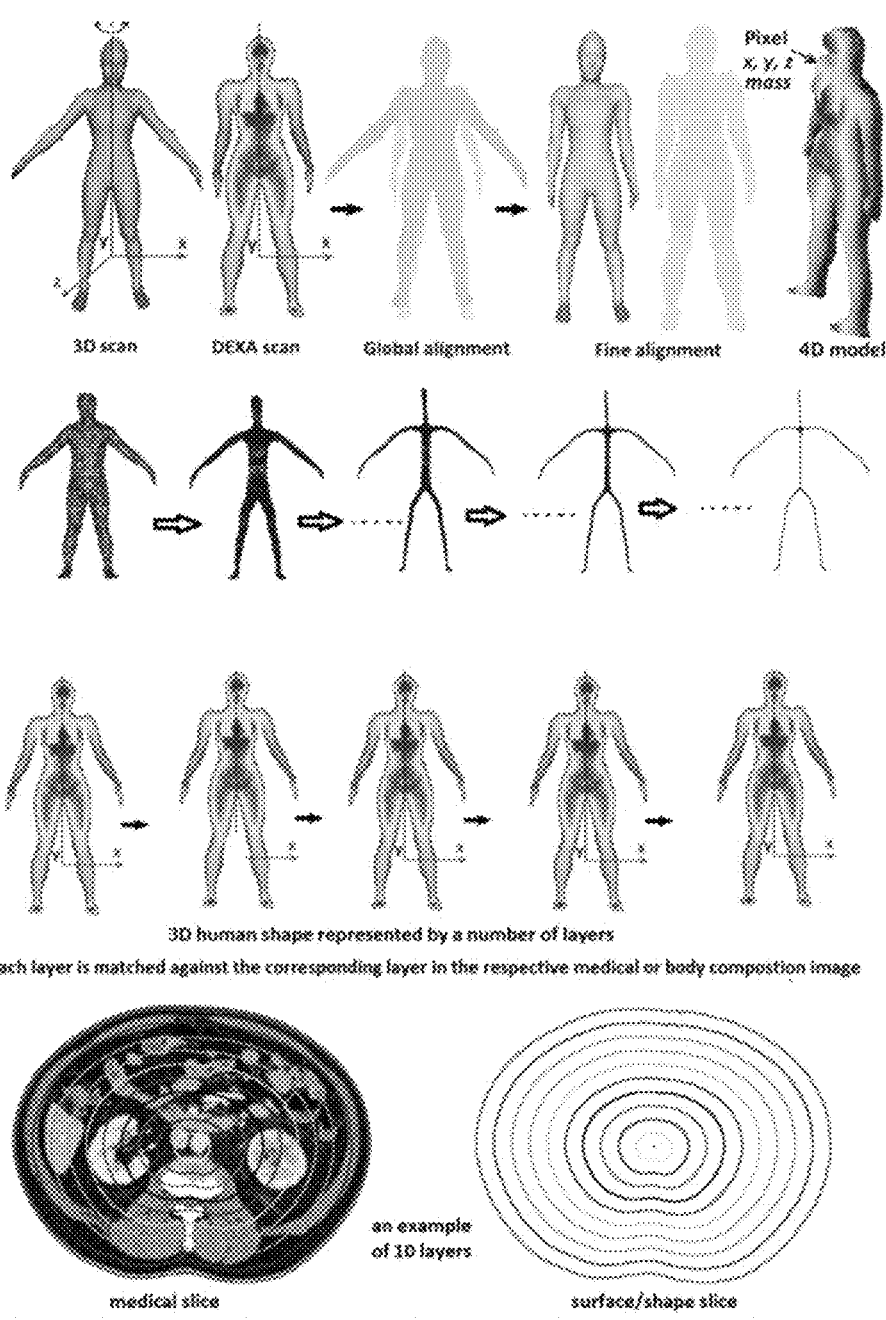
Fig. 3: The three rows of graphs above represent an example showing one of the processes developed to create a 4D version of digital quantum human model.

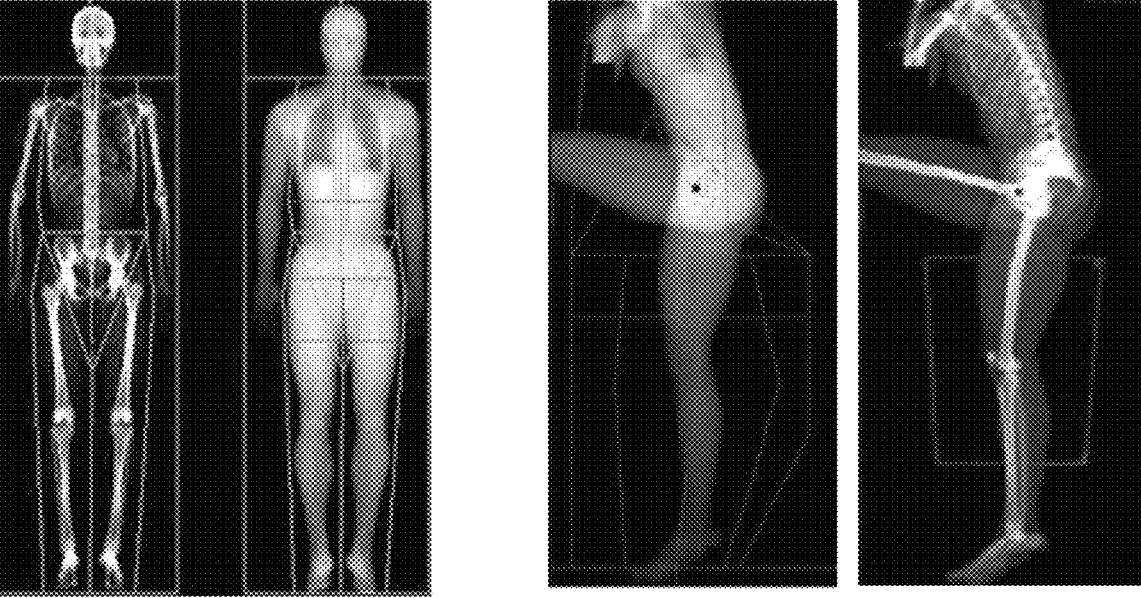

Current DEXA scanning methods                    Proposed additional DEXA scanning images and methods

Fig. 3A: Left is a classical medical image captured by a GE lunar iDexa scanner. In the absence of an MRI, an optional additional scan is proposed in this inventions to form a more accurate quantum digital human.

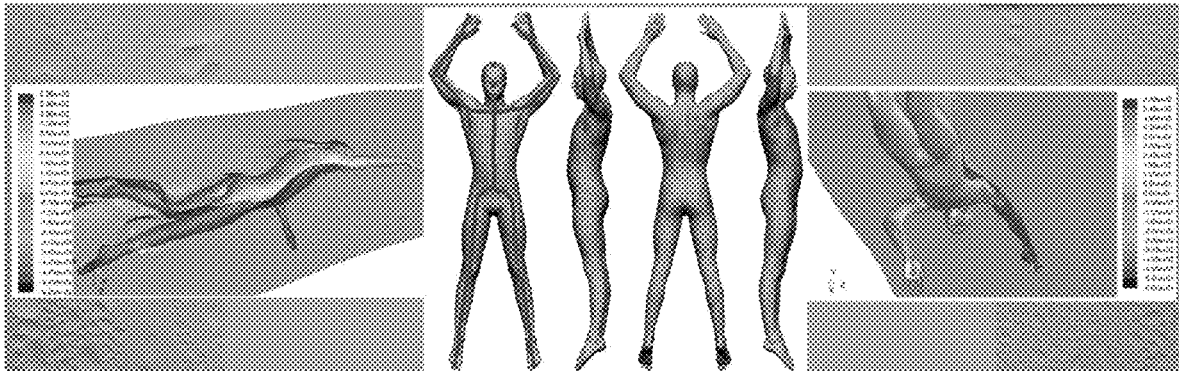

Fig. 3B: An example of a digital quantum twin of an elite swimmer in an actual movement analysis procedure

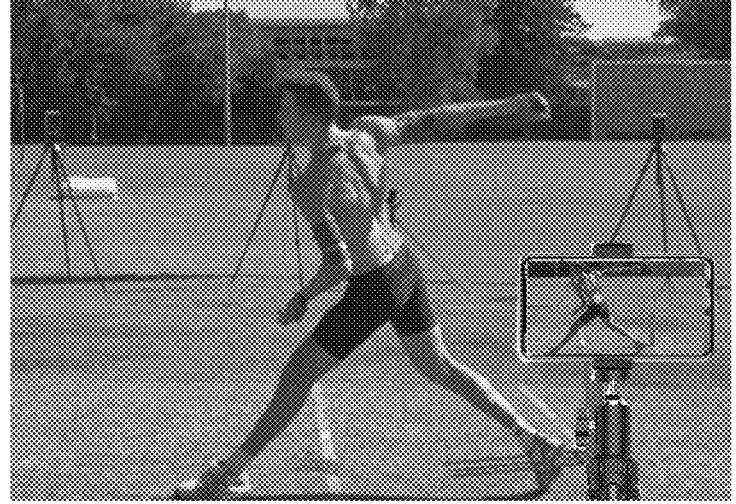
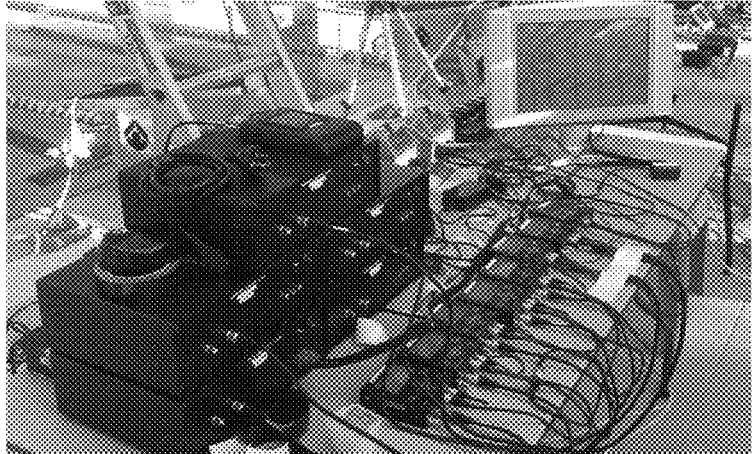
Fig. 3C: Two examples of data collection system invented for the development and testing of a digital twin of elite ballers and swimmers. Standard cameras and Smartphones were used for data collection and processing.

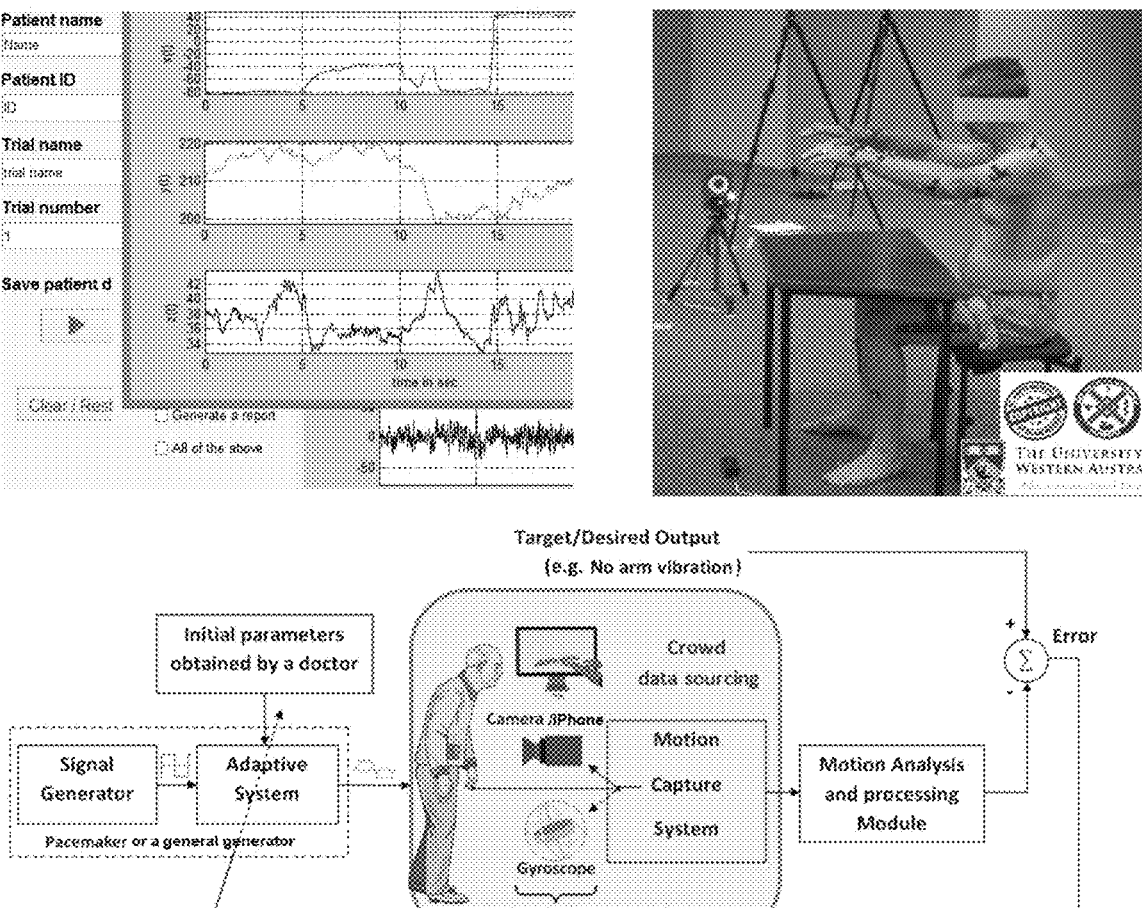
Fig. 3D: An example of data collection system developed to collect a movement data of a patient with Parkinson's disease and generate a medical report.
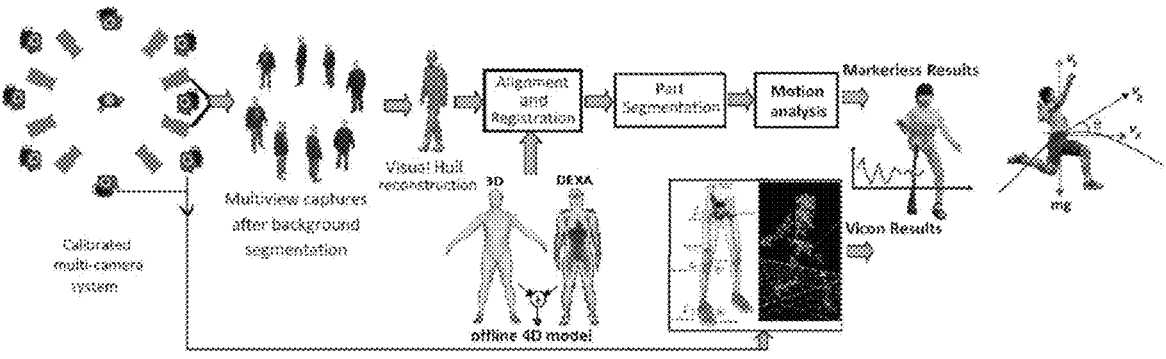
Fig. 4A: A block diagram describing the integration of a digital twin of human subject within a clinical or a sport analysis and assessment system.

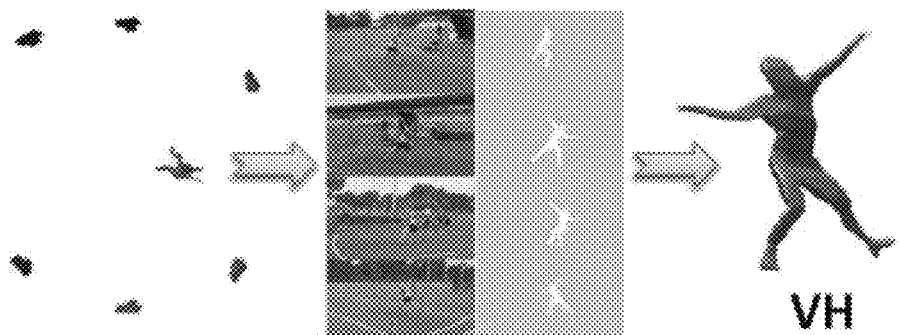
Fig. 4B: An example of a marker-less system with multiple cameras and videos where an abstracted visual hull of the subject was reconstructed to inform the motion analysis.
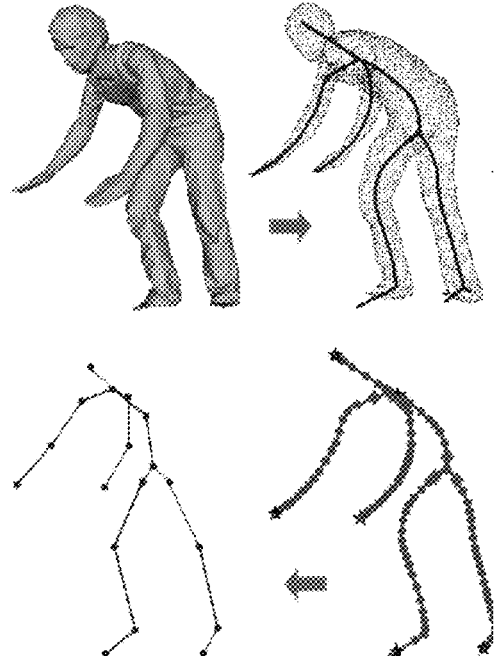
Fig. 4C: An example of an accurate visual hull (VH) of an actual Parkinson's patient and developed optimization processes to fit a skeleton into the visual hull.

Fig 4D: Some of the fitting and optimization process where the process developed to divide the body into different nodes, links, segments needed to inform the digital twin representation.

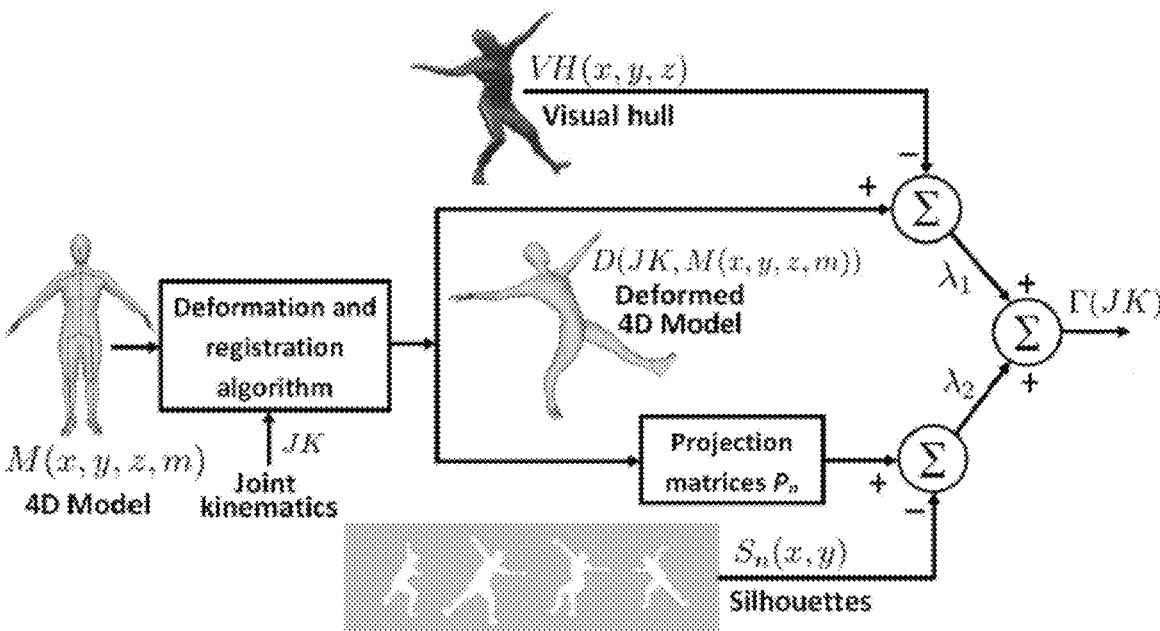

Fig. 4E: A block diagram showing the optimization and fitting process to steer, deform and align the 4D digital twin model to multi-view data its anatomical joints together with kinematics and kinetics data.

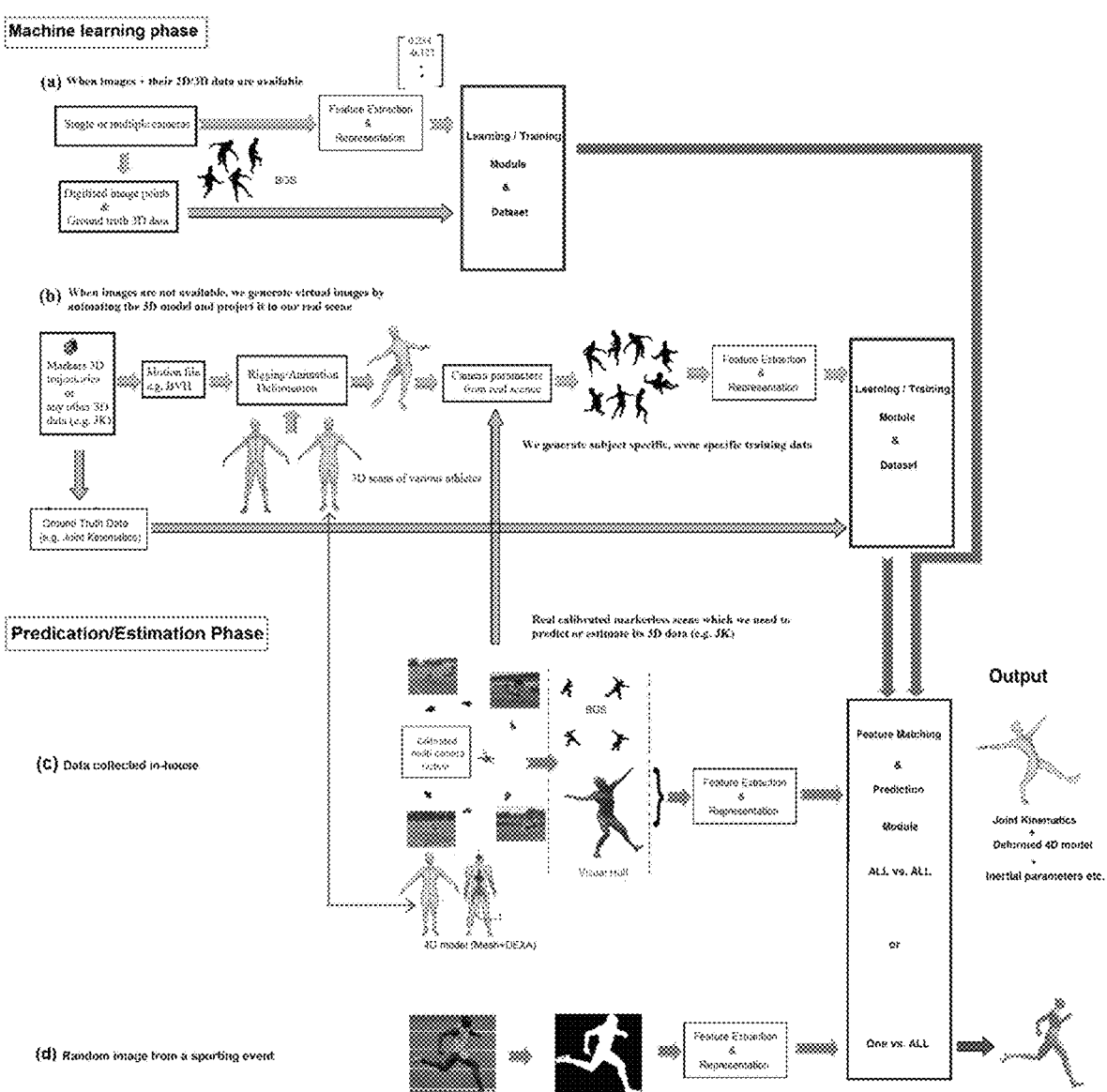
Fig 5. A block diagram summarizing the various computer vision and machine learning processes. The digital twin model is a key element in having highly accurate motion tracking and analysis.

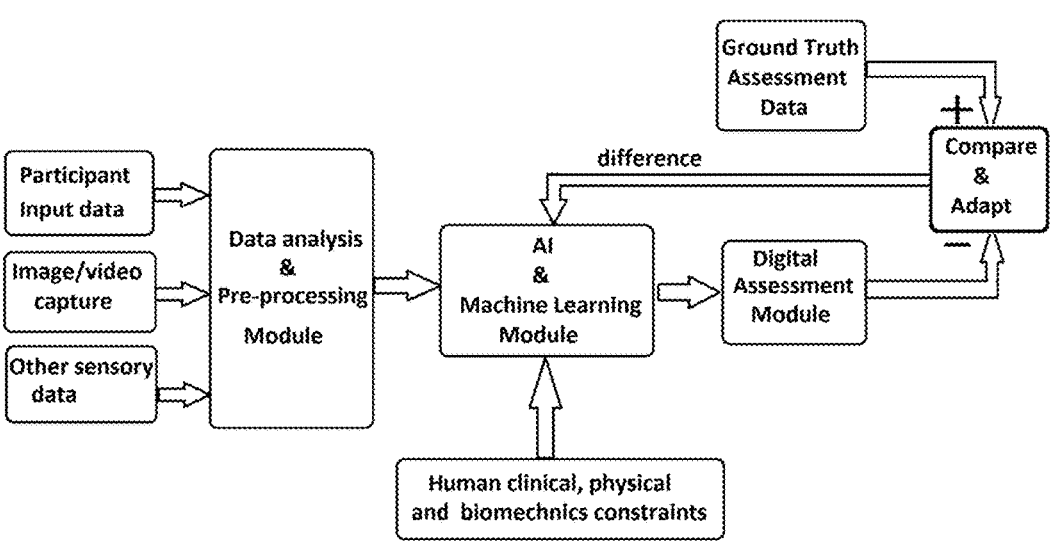
Fig. 6: Computer vision and machine learning system developed to learn and achieve the same outputs and assessments as a clinical health assessor or a sport biomechanist.
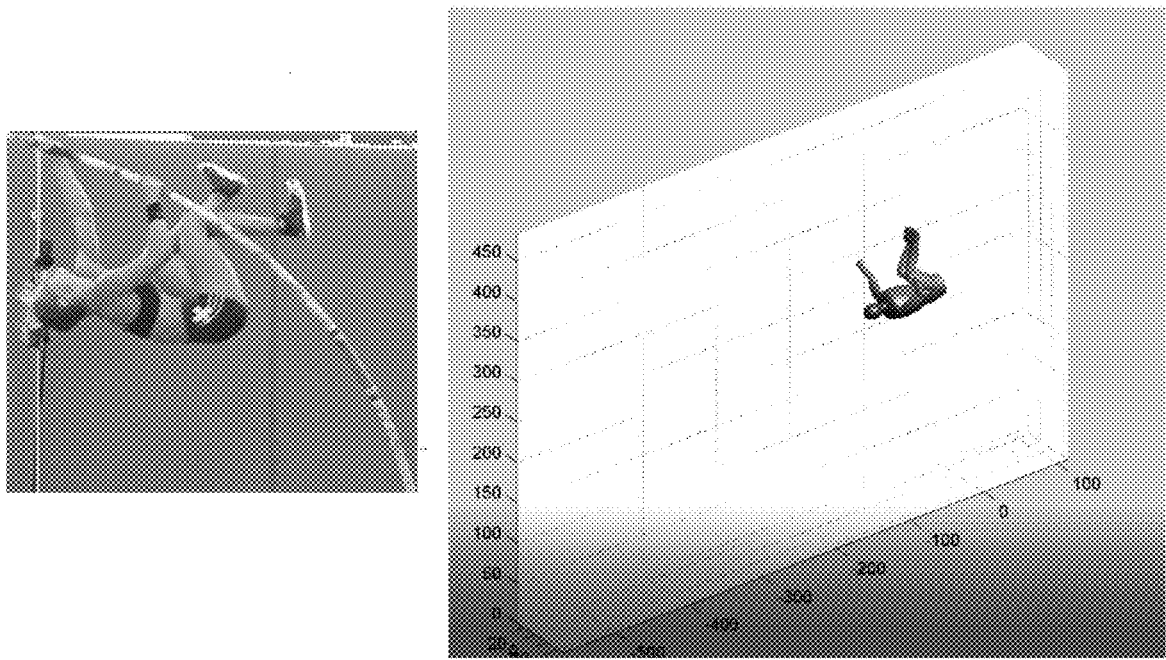
Fig. 7: An example of a simplified digital twin model of a human being used in sport.

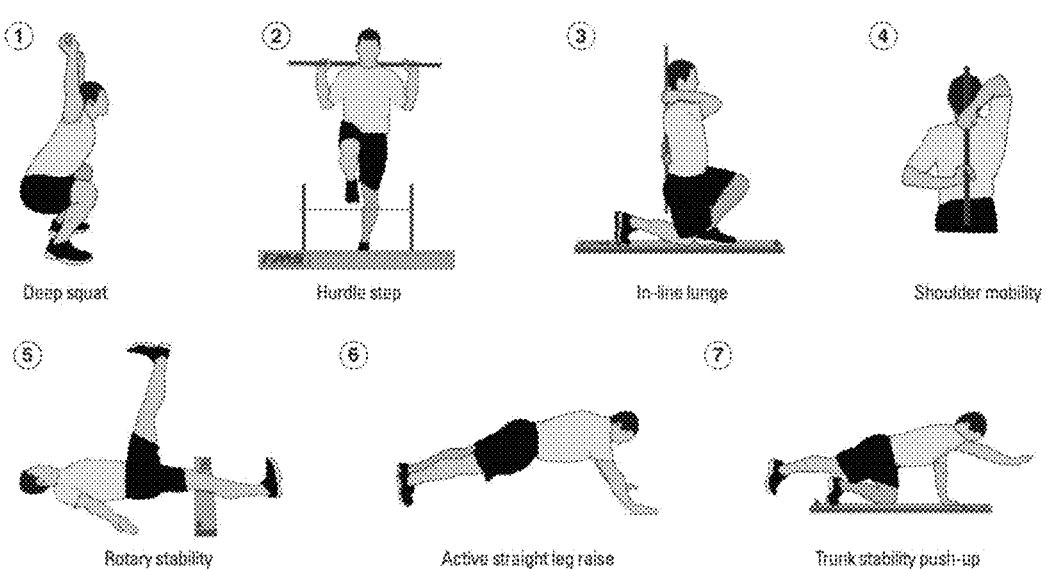
Fig. 8A: Standardized movement commonly used in functional movement analysis
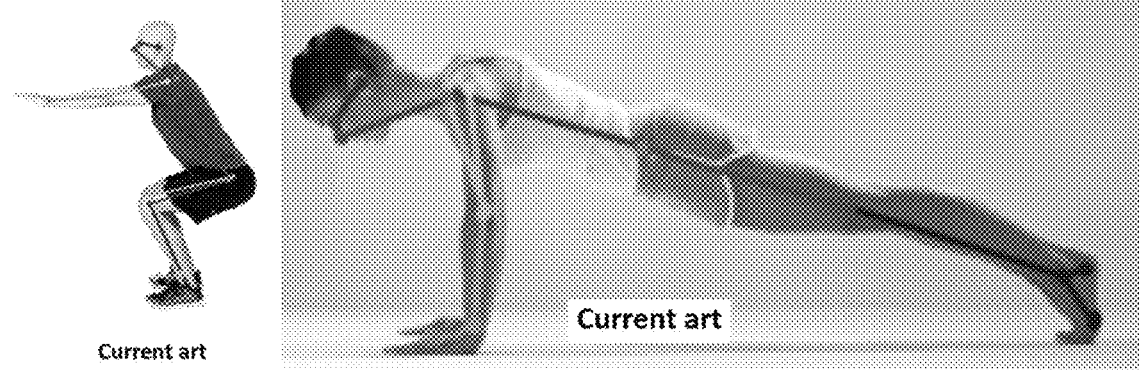
Fig 8B: Existing art uses 2D joints to analyse and assess movement, which would provide inaccurate ill posed outputs.

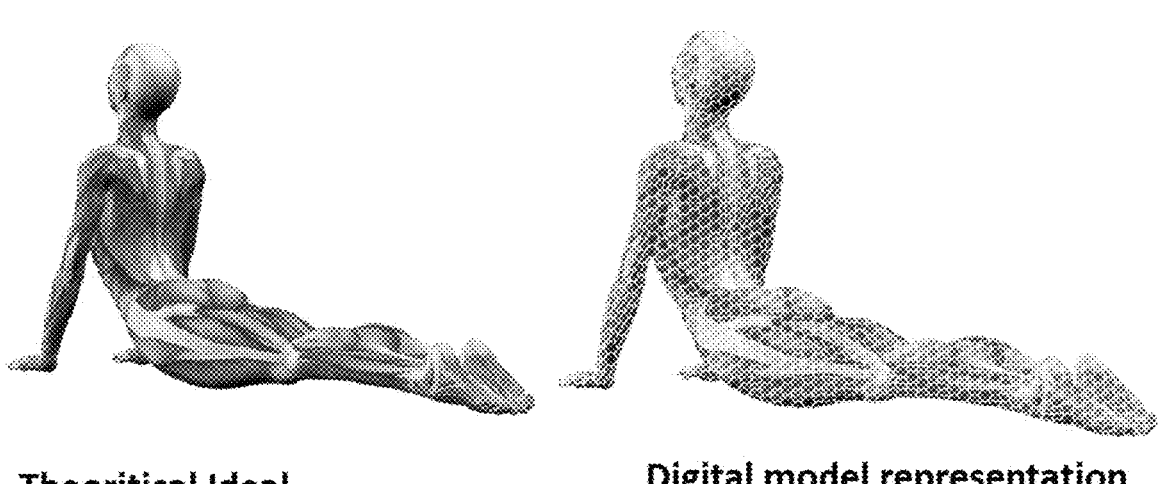

Theoritical Ideal    Digital model representation

Fig. 8C: an example of a human theoretical ideal representation and its digitized quantum equivalent representation terms are considered by this application only.

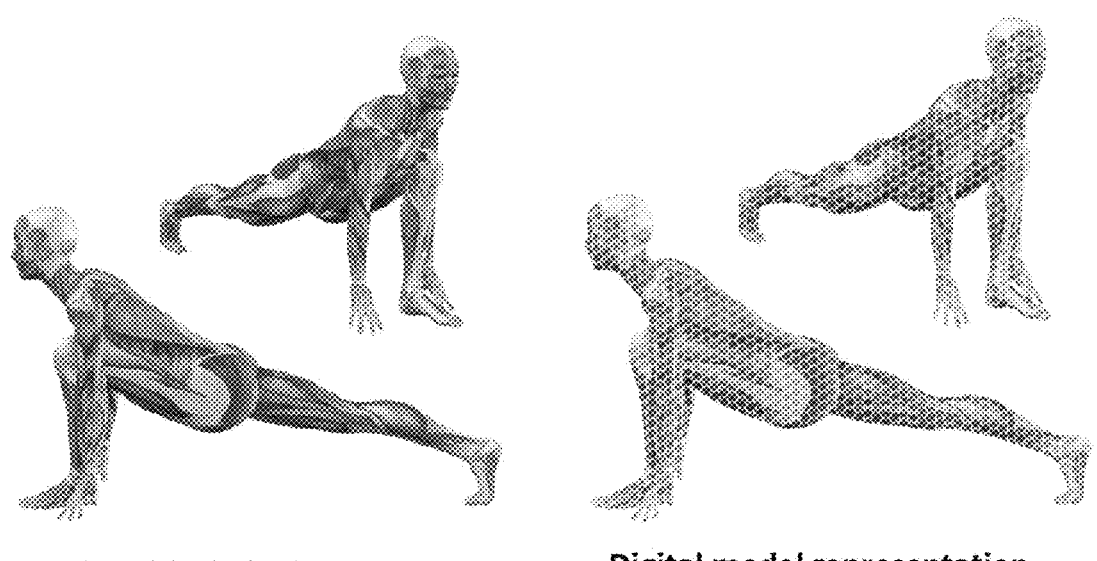

Theoritical Ideal    Digital model representation

Fig. 8D: another example of a human theoretical ideal representation and its digitized quantum equivalent representations. The invented system handles and model  multiview multi-tensor data

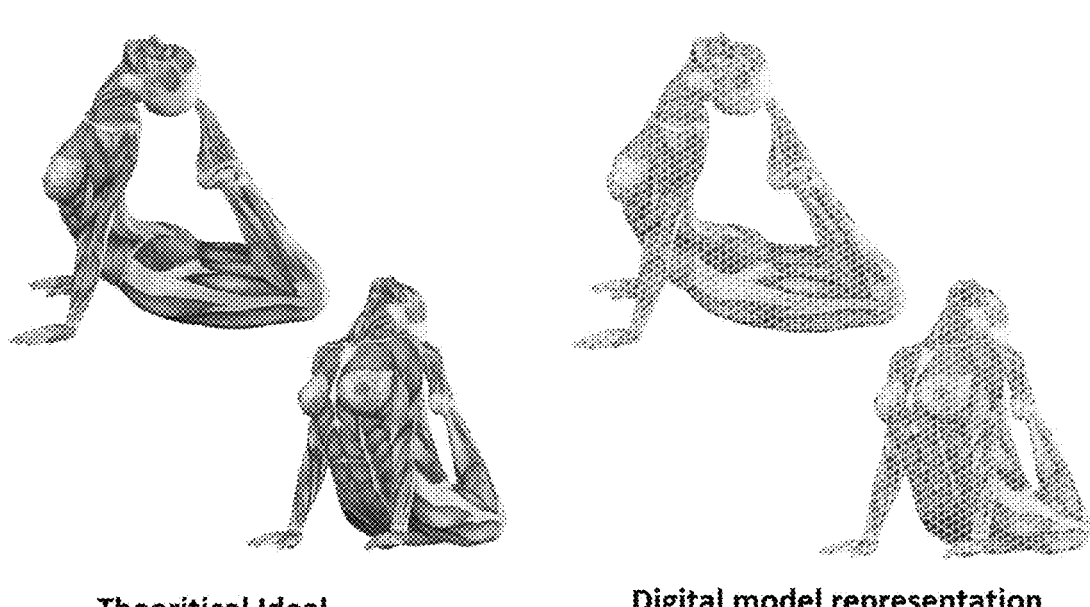

Theoritical Ideal          Digital model representation

Fig 8E: another example of a human theoretical ideal representation and its digitized quantum equivalent representation and the body parts (e.g. muscles) involved the specific pose .

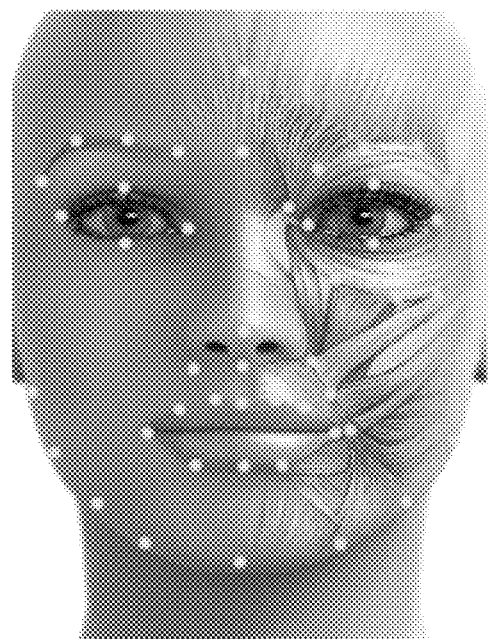

Fig. 9: An example showing the underlying anatomical model provided by our innovative digital model which accurately model and assess facial movement analysis and other related disorders (e.g. in speech).

TRACKING, ANALYSING AND ASSESSMENT OF HUMAN BODY MOVEMENTS USING A SUBJECT-SPECIFIC DIGITAL TWIN MODEL OF THE HUMAN BODY

CROSS REFERENCES TO RELATED APPLICATIONS

This patent application claims the benefit of U.S. provisional application No. 63/226,078 filed Jul. 27, 2021, and the Australian standard patent application Ser. No. 20/222, 04095 filed on Jun. 12, 2022, which claims the benefit of the Australian provisional application No. 2021901399 filed on May 12, 2021. *All of the above applications are incorporated by reference herein and the* WIPO control access codes for the Australian patent applications 2022204095 and 2021901399 are included.

FIELD OF THE INVENTION

The present invention relates generally to tracking, analysing and assessing the movement of a body using a novel digital, quantum twin model of a body, referred to as the quantum verse.

The present invention will be described with particular reference to tracking, analysing and assessing the movement of the human body using an accurate digital twin model of the human body (the quantum-verse), comprising digitized static and dynamic multi-dimensional elements, particles, data and modules of the human body and its clinical, physical, anatomical and biomechanical characteristics.

The global objective of this invention are: (i) to provide a novel clinically, physically, biomechanically and anatomically valid digital dynamic twin model of the human body and its particles which is developed and derived using an accurate 3D human shape integrated with clinical, physical, anatomical and biomechanical characteristics of a human body. One aim is to replace the existing traditional inaccurate models currently being used in the field of human movement and movement assessment, and (ii) use the digital dynamic twin model of the human for accurate tracking, estimation and assessment of the human movement dynamics such as the human posture including movement patterns, positions and orientation of each and all body segment, bone, element, and body rigid and non-rigid particles, and (iii) to develop novel systems, methods and applications integrated with the digital human model to target health, fitness, physical activities, rehab, functional movement assessment, range of motion assessment; musculoskeletal assessment, injury prevention and sport.

It will be appreciated that the invention is not limited to this particular field of use, it may be used in respect of bodies of other things, and for performing an analysis for additional and/or alternative purposes or analysis, or decisions or scores or diagnoses derived from the assessment of at least human movements.

It will be appreciated that the invention is regarded as a device and methods representing the collection of various approaches and systems interacting alone or together and driven by inputs and data that are directly or indirectly interacting, controlling or affecting the movement of a human body including nervous, musculoskeletal, cardiovascular, pulmonary, endocrine, and integumentary.

It will also be appreciated that this invention relates to systems and methods for the capture, tracking, analysis and assessment of the human movements as a whole or in-part using novel, accurate digital quantum model of the human body shape and composition including the skeletal structure, integrated with state of art techniques in the area of computer vision, machine learning, and the body biomechanical and physical characteristics. Unlike existing approaches where abstracted and global movements patterns of a human subject are either determined or measured using sensors attached to the human body or via abstracted data extracted from videos including the image based 2D or basic biomechanically in accurate 3D dimensional joint locations globally and widely used nowadays, this invention derives and combines unique markerless (non-invasive or quasi-markerless) features of the human body particle movements in a video representing the biomechanics of the body shape and composition following quantum physics theories and include: (i) a formation combining the human physical shape, anatomical structure and composition into the actual movement paradigm and (iii) the creation of a multidimensional subject-specific movement module of the human.

A system with modules offering these functionalities is essential and critical in areas such as sport where a millimetre difference in a movement e.g. a jump or a hundredth of a second in a run can separate first from last in competitions.

In sensitive areas such as health, inaccurate clinical assessment of data derived from human movements can lead to serious risks. These led scientists worldwide to continuously search for new methodologies that can accurately analyse human motions and physical activities.

Different techniques have been tested for this purpose for decades but they still have several limitations. Existing gold standard motion capture and analysis systems use body markers and rely on models derived from a few cadaveric elderly males or a few living males; hence will have little relevance when applied to a population of different morphological characteristics. With recent advances in imaging technology, computer vision and machine learning, markerless computer vision research has proven to be a powerful tool that can respond to these limitations. Thus, one of the main aims in this project is the development of a novel digital human model and multi-dimensional markerless movement analysis system and methods able to accurately analyze and assess human motion in static and dynamic scenes. Unlike existing systems, this invention will be the world first to propose a typical human movement model in which the human body topology, body segments, body mass distribution and physically relevant movement patterns are combined to form a unified module named a digital twin of the human subject, the human quantum-verse.

SUMMARY

Our novel techniques in this invention are aimed to substantially supersede and replace the conventional and approximated approaches researchers and scientists have been using for decades (which in areas such as sport and clinical analysis was derived from few cadavers). The system will provide new knowledge in motion analysis, tracking and movement assessment space across multiple fields.

The invention as a whole aims to: (i) create a digital subject-specific twin model of the human and the human body, a quantum twin; (ii) identify, detect and extract unique markerless features representing the human body and its movement pattern in e.g. a video; (ii) integrate and constraint the physical and biomechanical characteristics of the human and the human body represented by rigid and non-rigid shape and composition particles into the movement paradigm and other human relevant motion analysis. A system with these modules and one that has these function-alities is essential and critical in areas such as sport where a millimetre difference in a movement e.g. a jump or a hundredth of a second in a run can separate first from last in competitions. In sensitive areas such as health, inaccurate clinical assessment of data derived from human movements can lead to serious risks. This invention will substantially improve human movement analysis, human behaviour analysis, generally human body modelling and will achieve the accurate assessments needed in diverse areas including sport, exercise, science and health applications.

BACKGROUND

Any discussion of the background art throughout the specification should in no way be considered as an admission that such background art is prior art, nor that such background art is widely known or forms part of the common general knowledge in the field in Australia or worldwide.

Quantum physics suggests that every object in the universe has a dual nature. A wave and/or a particle but it was hard to see both simultaneously.

In 2015, Fabrizio Carbone from EPFL managed to capture light as waves and particles simultaneously. The finding is still being argued, but the conclusion was that light was made of many different photons. Each of them behaved in a separate way, a wave or a particle. Depending on certain conditions.

The question would be, what about the human? In quantum physics, even an entire human being, under the right conditions, can theoretically act like a quantum wave, but obviously it is a very difficult object to study or model in that aspect using the same theories as those used for a light photon.

Based on these theories, one can argue that the human or the human as an entity can be modelled, quantized or digitized into various micro or large scale sequences, chains, particles, modules, representations to name a few, because one might be able to trace any of these back to either a particle or a wave and both form the main intrinsic ingredients of any object.

This application will concentrate on some of these ingredients with focus on understanding human body motion and health using a valid physical model of the human body following the quantum physics and theory of matters. The human quantum verse.

According to the WHO, scientifically published evidence and experience show that regular participation in appropriate physical activity provides people of all ages and conditions, including those with disabilities, with a wide range of social, physical, and mental health benefits.

Physical activity generates health benefits in two primary ways (i) through direct participation in the activity itself, and (ii) through communication, education and social mobilization. It is well understood that physical inactivity is a primary factor driving the global changes in chronic diseases. Researchers have proven that physical activity and sport proved to play a critical role in slowing the spread of chronic diseases, reducing their social and economic burden, and saving lives.

Globally, the most prevalent chronic diseases include heart disease, chronic respiratory disease, stroke, cancer, high blood pressure, high cholesterol, obesity, tobacco use, stress and diabetes. WHO reported that these and other chronic diseases are the main cause of death and disability worldwide, affecting not only elders but also many young people and those in middle age. WHO reported that the total number of people dying from chronic diseases is double that of all infectious diseases, including HIV and AIDS, tuberculosis and malaria. In fact and contrary to the perception, some of these chronic diseases primarily affect high-income countries, especially areas where physical and sport activities are limited. Another fact is that studies found that athletes are more likely to have irregular heartbeats than non-athletes.

While physical activity includes a wider range of activities than sport alone (e.g. at home or workplaces), direct participation in sport competitions even at a learning level or an entry level, is regarded as one of the most enjoyable amongst all, and therefore sports is regarded as a powerful means of motivating and mobilizing people to become physically active.

As a result of these impacts, governments started to work on implementing policies and encouraging people to increase their physical activity levels or organize public sport events for people to participate, but the question of what constitutes an appropriate level of physical activity with minimal risk still arises. Providing simple but effective physical activity guidelines and recommendations to the public is essential but can be difficult because of the variety of exercise that can be undertaken and the number of possible health and potentially risk outcomes.

As an example, which reflects this, is the Musculoskeletal Disorders or MSDs which are injuries and disorders that affect the human body's movement or musculoskeletal system including the body muscles, tendons, ligaments, discs, blood vessels, nerves etc. MSDs are common health issue affecting nearly 30% of the human population. It is a costly problem for both people, government, insurance and businesses; thus, there is a need for novel and accurate techniques and technologies able to analyse human movements and provide the appropriate level of physical activity needed for each individual while ensuring minimal risks.

One of the broad objectives of this invention is to work out an accurate, optimal person-specific physical activity protocols aligned with the health and physical characteristics of the person and the standardised clinical protocols. This is important to guarantee that associated risks are avoided and their physiological response to exercise and fitness can yield substantial positive impacts in their general life and in their fitness-related benefits. Using existing human models and existing latest approaches to provide optimal physical activity plans is inaccurate. The use of current methods to assess e.g. movement dynamics in these person-specific plans over time to achieve these targets is not possible. Existing approaches abstract the human body by formulas or data of biomarkers with limited degrees of freedom (e.g. joints) and this type of approaches are considered amongst the technique that fits all subjects. This invention also aims to a use accurate movement assessment to develop subject specific imbedded electrodes on garments that can be positioned to stimulate key muscles throughout the body or noninvasively overcome symptoms or help with body implants or adjust parameters of the electrodes or the pacemakers or generally neuromodulation.

Scientific evidence indicates that moderate physical activity of e.g., brisk walking is sufficient to produce many health benefits. Published reports suggest that 30-60 minutes of moderate-intensity activity, 3-5 times a week benefits blood pressure and hypertension, blood lipids and lipoproteins, blood coagulation, cancer, depression and anxiety. However, more monitored activities are necessary to reduce other causes of mortality due to e.g., cardiovascular disease, obesity, and type 2 diabetes. This shows the necessity of a person-specific physical activity tracking, and assessment system integrated with programs and clinical protocols, that can achieve the intended goals and with minimal to zero risk when compared to existing approaches. This invention is developing a novel system with various modules to achieve that. The system is summarized (FIG. 1).

THE INVENTION

In this invention and given the substantial expertise of the inventors in the computer science and sport science, exercise and health fields in addition to their highly regarded prior arts with well-known sport and health organizations such as Swimming Australia, Australian institute of Sports, and Cricket Australia, in addition to the global aims mentioned earlier, the main aims of this invention are to: (i) create a novel dynamic digital subject-specific twin model and representations of the human body, a digital dynamic twin and (ii) identify and extract unique markerless (non-invasive) features representing the human body, the finite human body dynamics, and the human movement pattern from e.g. a video or any other human movement data (iii) integrate and constrain the physical and biomechanical characteristics of the human body into the digital human twin and the movement paradigm, (iiii) develop novel movement analysis and assessment systems and methods using the tracked human and the reconstructed human movement patterns, (iv) refine and match the movement patterns against additional subject-specific clinical, physical, and biomechanical human dynamic constraints, (v) optimize, track and monitor the assessment of all outputs over time and devise subject-specific plans to target one or more of the subject's objectives or clinical procedures including those in health, fitness, physical activities, rehab, functional movement, musculo-skeletal assessment, range of motion, injury prevention and sport performance enhancement.

The system is generally meant to target human movement tracking, assessment and analysis but with more focus into the physical activities and sport and their relevance in health, exercise, sport and science. Some of the standard assessment protocol will be considered within the physical activities and rehab sectors such as Functional Movements Screening (FMS), range of motion, musculoskeletal and injury prevention (MSI) and the health scores associated with each. Another is to target sport activities including coaches, coaching, trainee and elite athletics with subject-specific performance tracking and improvement producers and programs to monitor and boost their performance.

In sports alone, perfecting the estimation of precise stride rate or stride length and ratio or movement in general using a system able to provide real-time feedback like the one in this application combined with haptic and visual cues based on novel computer vision and machine learning is essential. In fact using the invented system to also analysis opposing athletes lateral weight distribution and movement, provide indicators on optimal change of direction, action and timing which are critical objectives in sport analysis as they improve performance and minimize injury at the same time and will get athletes to their natural peak quicker than ever and give them the confidence.

In order to achieve these many unique objectives from the inventive system, we divide the physical activity assessment programs into various categories depending on the participant module characteristics we built as shown in FIG. 1. The program or approach is like a prescription in which the duration and type of activity will be clinically and biomechanically constrained following the standardized and approved protocols in each field and the limits, agreements and scores allowed and identified in the health and science arts.

The same criteria are also extended to the field of sport science where trainee and athletic-specific models, programs and protocols are developed to prepare and guide a coach, trainee or an athlete to achieve an optimal or the best possible performance and monitor, assess and prevent injuries. So for example a protocol in swimming may have an overlap with the one develop for e.g. long jumps but each would require different module of the system shown in FIG. 1. This is because in addition to the dynamic digital twin human model, the underwater movement analysis and assessment requires techniques enabled with data derived from computation flowed dynamics where the methods concerning long jump requires assessment that need data derived based on e.g. ground reaction forces and computational aerodynamics.

In either of the above example cases, the developed overall system is capable of dealing with and processing videos consisting of humans and any other measurements and assessments data either acquired in the laboratory or in the field. In each case, motion analysis can be done utilizing data acquired via sensors (markers), videos or other similar markerless data, or a combination of both or as simple as a stream of movement data stored on files or any other type of storage together with the required subject-specific information.

Some examples of the output measurements obtained from e.g. a video by the invented system integrated with the developed dynamically tracked digital twin human model can be outputted for the whole body or part or cluster of it include: positions, orientations, forces, moments, inertia, pressures, muscle strength, to name a few. These output data will be much more accurate and valid over the same ones (if any) provided by current approaches since existing approaches use only abstract or simplified biomarkers (e.g. joints) of the human to predict one or more of these outputs. For some clarification and the difference between the invented approach and existing ones see FIG. 2B and FIG. 8B.

In order to highlight the importance of the invented system, most of the existing techniques are laboratory based or derived from data collected in laboratories, but due to the rapid advancement of powerful computing systems such as those on standard home computer or smart devices such smart phones, Human motion analysis and assessment is now becoming a powerful recognition, investigative and diagnostic tool in various fields such as surveillance, sport and health not in labs but in public too [2].

Traditional motion analysis have relied heavily on data extracted from digitizing a video sequence of a person's motion. Recent advances in microelectronics have resulted in the development of new 3D opto-reflective motion capture systems and highly accurate inertial Micro-Electro-Mechanical sensors (MEMS) [3]. Opto-reflective and MEMS based systems are regarded as the gold standards in motion analysis and achieved good results when applied to motion and performance analysis in clinical and sport setups [4]. The typical use of these invasive or marker-based systems is e.g. to derive the analysis of body kinetics and joint kinematics. Although they are considered to be effective; little is known of the exact factors making one motion analysis technique better than another [4].

With rapid advancements in imaging sensors such the standard photo capturing cameras including those on smart devices, many vision-based systems have recently emerged for human motion analysis. The accuracy of current systems varies with several factors [5]: (i) the number of cameras used and their configurations in the scene, (ii) the representations of the visual data, (iii) techniques and models used.

Among the recent systems, markerless motion capture and analysis systems have received little attention from research communities especially in the clinical assessment and sport fields. This is due to the inherent challenges faced in tracking and estimating the motion of a subject in dynamic scenes and the complexity faced in deriving accurate kinematic of the or body models [6, 7].

Various approaches are developed to assess human movements from videos or similar data, but the assumption that e.g. (i) a two-dimensional (2D) information such as 2D position of a human landmark or approximated joints predicted from in an image, or (ii) approximate 3D positions estimated from few 2Ds or from multiview, the assumption is that any or all of these can replace an actual 3D position and 3D joint model of a human body joint is totally incorrect and will lead to inaccurate assessment.

It is currently not possible to identify or define the complete optimal solution for a given physical or motor activity. For a complete optimization of human motion, dynamical systems theory requires that mathematical models must incorporate a broader, wider range of organismic, environmental and task constraints. These encapsulate why clinicians and sports medicine specialists need to adopt more individualized subject-specific clinical assessment procedures in interpreting why movement patterns differ from two different subjects with the same identical biomarkers being identified by current approaches.

The risky results of these approximate approaches can propagate over time. Our bodies over time and at some older ages do not work as efficiently as they were designed to and our ability to move through the most basic and fundamental movements can become compromised. If this ability to move efficiently goes unchecked and inaccurately assessed, there is a strong likelihood that our bodies will develop compensatory movement patterns, which can eventually result in lost performance and injury. However, by accurately assessing the quality of some of our bodies' basic and fundamental movements, we can help to ensure that we continue to move as efficiently as possible, therefore reducing our risk of injury.

The most critical issues of most if not all of the existing markerless motion analysis and assessment systems suffer from is that they all rely on methods and systems developed from data (mostly open sources or animation data) captured in strictly configured laboratories and setups and are not in actual real outdoor scenes or in-field.

Most of the markerless motion analysis systems rely on data acquired for e.g. animation, or action recognition or even for garments such HumanEva, Human3.6M, Muhavi, and Cesar [19]. Such data is not suitable to derive or develop an accurate physical assessment protocols for health or sport. In fact, the subject-matters, the subject-specific digital human with the characteristics we (e.g. the human physical and body segments carrying out the segment mass compositions) are not used by an existing movement analysis system. They either considered as labels, elements or blobs (e.g. a cylinder model per each), but none of the existing approaches modelled each segment as an actual human body module that differs from a person to another. [016] another critical thing in the existing motion analysis arts from videos or similar data is that they ignored external forces affecting the human body movement and movement pattern. The predicted 2D or even 3D joints from a video do not reflect e.g. forces due to air (e.g. in running), water (in swimming), or additional light weights therapies use as a load for a person can exercise with to correct a posture or help prevent a future injury.

This Invention tackles the challenges faced by existing marker and markerless based movement analysis systems including those recently published methods that use 2D joint positions (or approximate 3D joints) as features or biomarkers assuming these can fully explain a human movement pattern, analysis and assessment. The invention, supported by practical work and experiments done at major sport, exercise and health organization (including Swimming Australia, Australian institute of Sport, Hospitals, University of Western Australia to name a few) will re-define the human movement paradigm and steer it to much more accurate and valid approaches.

This invention develops, novel motion tracking and analysis systems and methodologies derived from various data including on field data. The invented approaches are constrained by a number of human characteristics including accurate clinical, physical and valid biomechanical body structure data and constraints. The preliminary tests applied to on-field datasets that are collected in collaboration with major sport and health organizations such as Swimming Australia, Australian Institute and superseded those reported in the state of art and strongly support novelty of this application [7, 8, 11] [T1, T2].

The test has proven that technological innovation applied to health, sport science and coaching applications is playing a progressively more important role in the effective preparation of athletes and minimizing injury. The ability to quantify and visually present and assess a 3D movement patterns together with the impacting forces and moments of a human or elite athletes is essential for monitoring technique changes. It forms a critical input for methods related to e.g. range of motion, Functional movement screening or musculoskeletal assessment and the relevant scores or to optimizing athlete performance. Likewise, the ability to collect this data on key participant health rivals (as an ideal healthy participant) is of immense importance.

Currently there is no non-invasive system available to athletes and coaches anywhere in the world that can do this accurately and reliably during training or during a live competition using the accurate participant specific Four-Dimensional Digital Movement Model of a human (4DDMM) invented in this application. In some instants we will refer to it as 4DDMM or as "Digital Human", or generally NDDMM model when dealing with or adding additional human specific datasets including but not limited to wearable data, emotion data, medical history and treatment data, historical data, or speech driven or extracted analysis.

This invention leverages off the world class markerless motion analysis technology developed in the past 10 years. From a coaching perspective, the benefits are twofold. First, this technology will allow for high quality 3D kinematics for the whole body or part of it. This includes but not limited to joint angles, velocities and accelerations, forces, moments, inertia and 3D animations (for visual feedback) to be produced from training or competition-based video footage.

Although the invention can functional in marker (invasive) based system, but in many instances this is performed in a non-invasive manner and in a timeframe that is dramatically shorter than traditional methods. A further leading advantage is that the machine learning approach proposed enables physical and sports technique matching, where a video of other athletes (past or present) or an ideal and healthy physical figure, can be reconstructed to produce a 3D animation that can be overlaid onto another person for direct comparison or to design programs needed to achieve optimal outcomes and injury prevention. Another output of interest is for coaches to contrast training or competition footage of the same person or athlete over time.

This information is further expanded using additional data entered or supplied by a participant or athlete-specific inertial data for kinetic analysis (joint forces and moments), which has significant injury prevention. A validation pipeline is also developed to input data into a musculoskeletal modelling package (such as OpenSim) produce highly advanced analysis for optimizing the technical models of each individual participant. The benefit of the athlete-specific objective data in these phases of the invention allows for the individual optimization for people with disabilities and Paralympic athletes, where information that incorporates the 3D body shape (if available) in the analysis and inertial parameters are of primary importance.

BRIEF DESCRIPTION OF THE DRAWINGS

The methodology involved and described in this invention is best portrayed within the following diagrams in FIGS. 1, 2A, 2B, 3, 3A, 3B, 3C, 3D, 4A, 4B, 4 C, 4D, 4E, 5, 6, 7, 8A, 8B, 8C, 8D, 8E and 9, and the short descriptions below and the detailed ones included with the figures.

FIG. 1 describes a compact overview of an example of a system of the invented device described in this application.

FIG. 2A, shows samples of an on-field, in-lab or at home movement and clinical data including wearables' data according to some examples described in the disclosure.

FIG. 2B, shows samples of the developed digital twin quantum human model of a person in a dynamic movement scenario according to some examples described in the disclosure.

FIG. 3: demonstrates the creation of a special case of a 4D digital model of a human using human shapes and human medical images (Digital Quantum human), according to some examples described in the disclosure.

FIG. 3A, presents and discusses the addition of a side view DEXA scans or dynamic digital radiography for an accurate digital quantum human model, according to some examples described in the disclosure.

FIG. 3B: presents a digital quantum human model and some analysis using computational fluid dynamic analysis in the case of swimming, according to some examples described in the disclosure.

FIGS. 3C and 3D: present two real world examples and applications of the invention integrated as a system or within a smart device, according to some examples described in the disclosure.

FIG. 4A to FIG. 4E show a number of procedures and systems devised within this invention for various data and various predicted human data according to some examples described in the disclosure.

FIG. 5. shows an overview of one of the proposed systems utilizing various types of human data according to some examples described in the disclosure.

FIG. 6: shows an overall computer vision and machine learning system developed to learn assessments done by a clinical health assessor or a sport biomechanist according to some examples described in the disclosure.

FIG. 7: shows an example of a heatmap representing quantum biomechanical analysis in sport according to some examples described in the disclosure.

FIGS. 8A and 8B: show examples of standard (existing) analysis and their limitations according to some examples described in the disclosure.

FIGS. 8C to 8E: show examples and applications of the invented quantum human body model and its anatomically relevant representation according to some examples described in the disclosure.

FIG. 9 shows another example utilizing the invented quantum human model in e.g. facial related movement analysis or disorders including speech disorders according to some examples described in the disclosure.

DETAILED DESCRIPTION

Certain details are set forth below to provide a sufficient understanding and clarification of examples of various embodiments of the disclosure. However, it is appreciated by one having skill in the art that examples described herein may be practiced without these particular details. Moreover, the particular examples of the present disclosure described herein should not be construed to limit the scope of the disclosure to these particular examples. In other instances, well-known circuits, control signals, timing protocols, and software operations have not been shown in detail in order to avoid unnecessarily obscuring embodiments of the disclosure.

FIG. 1 is a block diagram of a system 100 according to an embodiment of the disclosure. The system 100 includes a memory system 110, a controller 120, a computing means 130, a data input means 140 which includes a human (a participant) data, sensory data including images, videos and motion sensors, human relevant data 150 which includes any human dataset of any type and existing human movement data being gathered indoors and outdoors, Constraint standardized clinical, physical, ecological and biomechanical data of the human body in 160 required by the human (participant)-specific movement module in 170 to create the digital human in 180

The controller 120 comprises processing means in the form of a processor. The storage comprises read only memory (ROM) and random-access memory (RAM).

Sets of FIGS. 2A and 2B. Represent an example 150, but the example does not limit the generality of the human data as some data can for example age, height, weight, gender, health records.

FIG. 2A. provides some examples of various human movement data used in this invention including images, marker-based, and body shapes. Our invention uses various types of these data in the offline dataset collected for development, validation and testing.

The example depicted in FIG. 2B. discusses a clarifying method of the developed digital quantum human model of a person in a dynamic movement scenario. As seen the developed digital human twin surpasses existing art and will have highly accurate and meaningful results when compared to existing movement analysis arts. Existing arts abstract the human body while this invention derive a highly accurate and physically-meaningful movement model of the human which takes into accounts the forces (described by the arrows) affecting every rigid or non-rigid body particle with a mass m and 2D or a 3D position x, y, z.

The mesh and other data of FIG. 3 demonstrates an example of the combination and the deformation of a human data type (3D body scan in this case) and the specific medical image of the human (a body composition scan in this case), to form a four or more-dimensional (4D) quantum model of the aligned shape and composition. The example 4D model is the key element in this invention as it will be further combined with movement data in 170 to form the digital human. The movement now, in this invention, is no longer abstracted information or approximated 2D or 3D joint positions but a human defined by particles with movement positions that will allow in-depth finite element analysis type of human particle movements of a full (complete) body models with anatomical structure. We regarded the created digital twin human as a quantum type of representation of a human body where one quantum can (theoretically) have any number of features besides the 4D shape and mass information and distribution. From this invention we strongly believe that novel digital human processing methodologies in various fields and new inventions can be developed given the limitations and the less accurate models in the current art. The method in FIG. 3. is an example aimed to model a 4D quantum human using a 3D shape and a medical image such as static or dynamic DEXA scan or dynamic digital radiography. The alignment is then followed by modelling the body shape by a number of layers (skinned serious of image), each layer is then matched with its corresponding layer in the medical image and finally the human body shape and body molecules are modelled as a biomechanically valid digital human.

The example of FIG. 3A, shows body composition images acquired by a GE lunar iDexa scanner for 100, 150 and 170. Although the DEXA images are used to derive stat of art body composition analysis of the human body, however they still have several limitations, our invention will further use Dynamic Digital Radiography. One Approach to cater for the limitation is to acquire additional side view scans of the human and fuse the composition outputs and density with those obtained from the front dexa scan to form the quantum digital human 180.

An example of a digital quantum twin of an elite swimmer in an actual movement analysis procedure is shown in FIG. 3B and the heatmaps representation of the body interaction with water and the representation of forces and other affecting data obtained via computational fluid dynamic analysis.

Two examples of data collection system developed in this invention in FIG. 3C which shows marker (e.g wearables) and marker-less movement data needed for the development and testing of a digital twin of elite ballers and swimmers and can form parts of 140, 150 and 170. Smartphones were used for data collection and processing are depicted in FIG. 3D which is an example of a marker-based data collection system developed to collect a movement data of a patient with Parkinson's disease for the development and testing of a digital twin of the patient where movement assessment can be used to develop imbedded electrodes that can be positioned to stimulate key muscles throughout the body to noninvasively overcome symptoms or help with body implants or adjust parameters of the electrodes or the pacemakers.

The system in FIG. 4A shows an example of a 4DDMM (digital quantum human) 180 in a motion analysis scenario where 140 are a group of different cameras as an input means clarified further in FIG. 4B, anatomical and biomechanical constrained are also shown together with a simple depiction example of the analysis and the moving pattern (waveform). The system is not restricted to use multiple cameras or sensors but can be functional with a single camera or a senor such as those on smart phone. In other words, a smart phone can replace 140, 110, 120, 130, and 150, 160 can be stored in 110, or external to 100.

FIG. 4B Shows An example of a marker-less system with multiple cameras for data needed in 100, where an abstracted visual hull of the subject was reconstructed to allow for better alignment between the subject's digital twin model and their data including segmented images. Only the athlete was detected and segmented herein, and static subjects (including humans) were removed.

An example of 140, 150 can be an accurate visual hull (VH) of an actual Parkinson's patient in FIG. 4C. The invention developed optimization processes to fit a skeleton into the visual hull which is then used to initialize a valid 3D anatomical skeleton. This example also shows that it is possible to use VH as a representation of a human shape as part of a digital twin model of a person 180.

FIG. 4D shows an example showing some of the subprocesses with the skeleton fitting optimization process. As seen the process can be instructed to divide the body into different nodes, links, segments and finally 3D segments or surfaces allowing ten human body to be modelled with its digital twin representation in various forms to achieve 180.

The method of FIG. 4E shows an example of a method in which the 4DDMM (digital quantum human) is integrated of the human 3D joints then optimized to track and fit a movement of a person in a video frame or image of a person or against a group of images or a visual hull reconstructed from the group of images or videos in a multiview system implementing 140, 150 or 170.

The system in FIG. 5 summarizes most if not all types of human data including motion/movement data that the developed system 100 able to handle in and can be utilized in 140, 150 and 170. As seen the digital human twins in the outputs of the systems in FIG. 5 which form 180 and analysis of the invented system. The system 100 is developed and trained using various type of human data and motion dataset through learning processes using novel state of the art computer vision and machine learning algorithms and the clinical and biomechanical constrained by a human shape.

The system in FIG. 6 shows a 4DDMM (digital quantum human) being used in an example of movement assessment system using one of the trained Machine learned models resulted from the processes in FIG. 5. As evidently seen the full human and not an abstracted features or anatomically inaccurate keypoints or joints are used. The invented system 100 and the analysis facilitated by 100 in this application, is the world first since no equivalent movement analysis or assessment system is integrated of as a finite-element type digital quantum human model. It is a valid digital quantum twin of the person. All existing system including those used for elite athlete uses joints, total body mass and height. Best methods such as those in software packages in best sporting centres across the globe (such as OpenSim) still approximate the human model and not a subject-specific although it is the gold standards analysing software in clinical health (e.g. to assess musculoskeletal) and in sport. So, one can imagine a system with an accurate physical, anatomical and biomechanical subject-specific system such as the one invented herein is better than the gold standard system, thus any existing system that condense or derive the entire assessment process from joints from extracted from images or sensors (even if they are accurate) is still not an accurate system. The best way to explain this is to imagine two people with the same weight and same height and with the same joint positions. Existing systems will treat the two people equally (same height, same weight, and same joint positions) while the novel system we invented will use the digital 4DDMM human of each person to acquire the analysis and assessment thus treat them differently (they have different shape and different mass distribution). Even if shape is used in any existing system or the inertia as in OpenSim, the mass distribution of the body is absent and thus still and remains the major factor in the human movement analysis in existing movement tracking and analysis system.

An application of the system 100, is shown in FIG. 7 which demonstrates a real example of a Paul Vaulter and a corresponding 4DDMM model with some movement analysis described as a color heatmap.

The invention supersedes the standardized movement commonly used in functional movement analysis shown in FIG. 8A as it will used quantumly and biomechanically valid human model 180.

The invention will overcome the limitation of existing methods such as the example of the existing art shown in FIG. 8B, which uses 2D joints to analyse and assess movement, which would provide inaccurate ill-posed outputs.

The invented system in 100 supported by a number of examples demonstrating digital twin model representations of the human in FIGS. 8C to 8E and the and element quantum representation comprising various human shape and composition elements. Unlike existing arts, the invention considers the actual analogue or continuous model of the human body (theoretical), it then derives the digital representation using human elements (particles) detailed as follows:

FIGS. 8C to 8E present examples of a human theoretical ideal representation and considers the digitized biomechanically and biomechanically valid equivalent representation 180 of a human body and body anatomically relevant data, which are considered by this application only. Neither of these terms or modality have been used before in human movement analysis or assessments. The invention considers the actual analogue or continuous model of the human body (theoretical), it then derive the digital representation using human elements (particles).

As a summary FIGS. 8A, to 8E, show general examples of a movement sequence commonly used in functional movement assessment and musculoskeletal analysis or injury prevention. The figures also show how current arts abstract the human and its movement analysis by 2D joints, and how our invention deals with it and model the human movement using the digital biomechanically valid twin model together with the highlighted areas in the images where forces, muscles and movement assessment are done.

Another application of the invention is an example of a facial movement tracker in FIG. 9, where the underlying anatomical structure is considered, unlike existing vision-based trackers. Anatomical facial landmarks provide accurate representations and assessments of facial movement, facial health and speech tracking, recognition and analysis in the health sector and people with disabilities and speech disorders.

DETAILED SUMMARY AND PROCEDURES

The system and methods developed in this invention have immense implications for motion analysis across all physical activities driven health assessments and in sports. The strength of the developed machine learning networks and the design used in this invention revolves around the world-leading complexity of unique human relevant feature extraction and feature matching including the subject and the motion style unique features.

The ability of the system to utilize any prior or current motion analysis data, of any movement type, to complement and strengthen the machine learning training, validation and prediction phases can result in increased accuracy of the motion analysis for any movement skill being assessed.

For athletes, major applications for this project will focus on the technical events, in line with the targeted events/athletes. These events include javelin, long/triple jump, pole vault and hurdles; with targeted athletes in these events being the primary focus. The increased information associated with the kinematic analysis monitoring and associated specific body scans and inertial parameters are also crucial for optimizing the performance for athletes including Paralympic athletes that other systems cannot assess.

The deliverables of this invention will allow more regular evidence-based monitoring of technique within the daily exercising or training environment (DTE) and in a field-based or at home setting, allowing for maximum ecological validity of results. Consistent monitoring within the DTE of the targeted participants or athletes will allow for increased accountability for the clinicians or coaches and biomechanists, in line with the individual as personal or athlete/program objectives.

There is provided a device implemented as a system integrated with one or more representation or data or an input means enabling the system to capture, reconstruct or have access to a 3D shape or a 3D scan or any other 2D or 3D data captured by other existing technology and that can provide the human three dimensional (3D) shape or body composition (including predictive methods).

There is also provided another module of the device including an input means to handle data or representation enabling the system to capture, reconstruct or have access to medical or body composition images of the human subject.

Optionally, the human shape and medical or body composition images comprise additional data and information of the human body and can be optionally measured or delivered by any existing technology.

The device is integrated with novel computer vision, AI and machine learning techniques developed to automatically extract quasi-automatic features from the human data, process, align, register, animate, slice and model the human shapes and photographs together with their corresponding medical images to form a single representation of the human combining the body shape and medical image information in one module. Each layer in the module or each layer in a body segment of the module can be tracked, analysed and assessed individually or globally individually (see FIG. 3A)

The digital module requires a 3D human shape and its medical or body composition image(s) whether the medical images are 2D or 3D.

A mathematical model of the 3D human anatomical bone structure, density scores, hierarchy, connectivity and joints including joint rotation and allowable movements is developed. The development takes into account offline datasets of actual human shapes, medical images, and human anatomy.

Advanced optimization techniques are derived to fit the developed 3D anatomical skeleton to each human 3D shape while the corresponding medical image can be manually digitized to identify the same anatomical structure, however the human shape may come in a different pose from the one presented in the medical image.

A further optimization process is developed to link the fitted 3D anatomical human skeleton to the 3D human surface and shape. The process is further expanded to facilitate the deformation and movement of the human surface and body parts given the movement of one or more of the movements of any joints or bone of the fitted 3D anatomical skeleton.

An approach is then developed to estimate the mathematical transformation between the fitted 3D skeleton joints and bones and its corresponding annotated anatomical one in the medical image.

The transformation is then utilized within a convex optimization process to globally align the human 3D shape and its associated 2D or 3D medical or body composition images such that the skeleton joints and bones are matched and aligned and the global error between the 3D shape and the 3D medical images becomes minimal, or in the case of 2D medical images the projection of the 3D shape vs. the 2D medical images is minimal while constraining the smallest possible error between the joints and bones in all cases.

An additional optimization process is developed to fine tune the pose (position and orientation) of each joint and bone fitted to the globally aligned 3D human shapes such that the 3D human shape verse the 3D medical image reaches its optimal minima in addition to the global alignments of the joints and bones.

A novel computer vision approach driven by the 3D human shape and its fitted and refined skeleton is then developed to segment and slice the human body shape and its corresponding medical image or 3D medical image into slices and parts (see FIG. 3). The approach contracts the human shape in an iterative but highly constrained manner to reach its skeleton followed by a mathematical thin curve skeleton model of the human shape. The same process applied to the medical images.

Since the 3D human shape and the medical images are now co-aligned, each layer in the 3D shape represented by its 3D XYX position will now have an additional feature from the aligned layer in the static or dynamic medical images. The additional feature can be the corresponding point, particle, or cluster of fat, lean mass, bone or water. In other words a body mass value and a body mass classification leading to a digital human made of various layers, each layer can give certain number of points or clusters or particles, each of point, cluster, partial can have position, global and local orientation with respect to (w.r.t.) the whole body or w.r.t. any segment, bone, or joint in the body, mass, classification (fat, lean etc.). The classification herein in this example is only for clarification and simplification.

The process from to is repeated for each subject in the dataset such that one would have the human shape, and medical layers together with their 3D anatomical skeletons fitted, aligned, sliced, segmented and matched to form a single module named the digital human. Each subject will have a unique digital twin module of themselves.

Advanced machine learning networks and models are developed to learn and replicate the manually annotated joint and bone identification in the medical images. The process may include automated or semi-automated feature extraction processes and methods.

Advanced machine learning networks and models are also developed to learn and replicate the fitting of the 3D anatomical skeleton within the human shapes. The process may include automated or semi-automated feature extraction processes and methods.

Advanced machine learning networks and models are developed to learn and replicate the global and fine alignments between the 3D human shapes and their corresponding medical images.

Additional advanced machine learning networks and models are developed to learn and replicate the slicing and segmentation of the unified human body and medical images into a co-aligned layers and facilitate the creation of the digital twin model of the human subject and the relevant shape and anatomical information and data.

The machine learned constructed digital human model will be the main driving power in the subsequent human motion tracking and movement analysis.

In addition to the 3D shapes and scans and the medical images (such as DEXA/DXA scans or Dynamic Digital Radiography which is to the best of our knowledge never used before in human motion analysis), the offline dataset includes unlimited videos from single and multi-views of human movements in-doors and outdoors including athletes and patients and their movement patterns acquired by a state of art movement systems such as Vicon.

The invented system took advantage of this rich offline dataset and developed advanced computer vision, AI and machine learning to evaluate and analyse marker-based and markerless-based human data and data capturing systems. In order to do this, a number of computer vision and machine learning approaches are initially trained to detect and distinguish a person from the background. Unlike existing approaches, the system is trained to detect and segment only the person of interest given one or more classifications including being a human, dynamic (moving), the type and the expected speed of a movement and the type or a class of movement (to name a few). For example, gait analysis detector has a different class or classification to a long jump detector, at least each has a different movement pattern. In other words during the training of the machine learning models, these types of classes are parts of the input and if they are absent or set to null the system will consider the general human detection, segmentation and tracking scenario. This applies to the case of marker and marker-less types of human data. The processes may include automated or semi-automated feature extraction processes and methods.

In the case of marker-based system such as those with opto-reflecting (such as the Vicon system, https://www.vicon.com/), Bluetooth, Wi-Fi, Gyroscopes or other sensors that can provide and define human motion, the invented deformable digital human module can be driven and deformed using these sensors data and subject to its physically valid anatomical bone skeleton structure. Accurate evaluation, analysis and assessment can then be evaluated from one or more frames of the deformed digital human module in the motion.

In the case of markerless data or markerless capturing systems where only videos, or a sequence of video frames or images are presented, the invented system as a whole will:
  a. Detect and identify a human subject in a video or images.
  b. Segment the human shape from clutter and backgrounds (whether indoors or outdoors)
  c. Fit a 2D human skeleton on the fly into the segmented human image, or a 2.xD for depth images
  d. Use mutual information and correspondence between moving pixels and segments in the current, before and after video frames and correct for dropout and achieve robust segmentation and tracking.
  e. Optimize and fit a subject-specific valid 3D anatomical skeleton to the segmented human given their 2D or 2.xD skeleton.
  f. Align the digital twin (the digital human 3D shape and medical image module) to the segmented human in each video frame.

Once the digital twin model is fitted to each segmented and tracked human in each frame in a video, human movement analysis can be evaluated (for the first time in the movement analysis art) using not only human joints but also using digital partials representing the human digits shapes, positions, mass, and classifications.

The analysis and assessment using the developed digital human in this invention is the first of its kind in the space of human movement, human physical activity and clinical analysis and scoring, human body injury and risk assessment, and sport performance analysis. The system uses fine and highly representative and physically meaningful features of the human body and its anatomy unlike any existing technology including state of art and highly sophisticated systems such as OpenSim which is driven by joint positions and a couple of abstractions of the of the human form such as the height and total body weight. The best in existing art assumes even distribution of human composition and no attempts to align a human shape to its corresponding medical or composition image to form a valid digital module eagerly needed to steer existing approaches and systems to a new and highly accurate path.

SUMMARY OF THE INVENTION

According to an aspect there is a device for tracking, modelling, analysing and assessment of a human body movement or a specific human body part; the device comprising:

a storage storing a dataset of diverse human data comprising one or more of imageries, videos, shapes, movements, motions, forces, moments, and relevant human health, physical, anatomical, clinical or biomechanical data of a full human body or a part thereof;

a computing controller integrated with storage for storing electronic programs and instructions for operating the controller and executing specific applications, and processes to process one or more of the human data and creating a deformable, dynamic, scalable, digital twin module of the human body co-registered shape and composition and its movement patterns and movements limitations constrained by the human body anatomical, physical and biomechanical characteristics, to form a digital quantum model of a human and a quantum human graph;

the creation processes of the digital quantum human twin comprising a computer integrated with;

(i) computer vison, statistical and machine learning models developed to facilitate slicing, matching and alignment of the human body shape, parts, data and images and its corresponding medical images, scans, particles, forces, moments, kinetic, kinematics and external environmental affecting factors, (ii) a storage storing the developed digital quantum human twin and;

(iii) input operable to capture or receive one or more of the human movement data, human body photographs, frames, videos including audio, depth, static and dynamic shapes, or other sensory data or predicted human data;

the developed digital quantum human twin is digitized into particles and is optimized in a form able to facilitate its integration and application in desktops, smart devices and systems-on-chips, process the captured or received input together with the developed digital human twin and an offline dataset to facilitate accurate tracking, analyses and assessment of the human body movement or a specific human body part and generate an output;

the output can be real-time or non-real-times (or offline) and includes evaluation, analyses or assessment of one or more human movement patterns and any driven criteria, score, indicator, performance, forces, inertia, angles, stress, twist, speed, acceleration, orientation, momentum and risk of the body as a whole or in-parts; communicate the output;

wherein the data is pre-processed and inspected subjected to standardised clinical, physical, anatomical, biomedical and biomechanical constrained and limits relevant to the specific human body and its digital twin using advance statistical techniques and/or machine learning techniques and/or AI techniques to score each specific data type and its contribution in the analysis and movement of the human body or part thereof.

In an embodiment, the input can be marker or markerless data, information, formulas or features or a mathematical representation extracted from imageries, shapes or videos of the human body or a part thereof and the output can be the human body or part thereof, speed, acceleration, angles, joint angles, forces, joint forces, moments, joint moments kinetics, kinematics, or other analysis or assessment derived from one or more resource and include physical, clinical, health and sport performance assessment.

In an embodiment, the input can be invasive, non-invasive or other external input or subjects or weight or forces or collision affecting the human body and its movement and contributing to the analysis and assessment of the human body, or a part thereof.

In an embodiment, the assessment and analysis processes comprises output performed by at least one computer vision (CV) approach, machine learning (ML), and/or artificial intelligence (AI) model.

In an embodiment, the movement of the human body being assessed belongs to a category or a group or a class of bodies and movement patterns, and the database comprises details of a plurality of different movements of the same or different human bodies belonging to the same, and/or a similar, category or group or class to that of the human body movement being analysed and assessed using the digital human twin.

In an embodiment, the human body and movement data and/or information comprises one or more of human motion or movement marker and markerless data, videos, photos, multiviews, full and/or partial body shapes or 3D surface scans, anthropometry, characteristics, attributes medical body composition imaging and health data, medical epidemiological and physiology information.

In an embodiment, the device comprises a display for displaying a user interface, wherein the controller is operable and guided by electronic program instructions, to communicate the output by displaying the output via the display depicting a visualization of the analysis and assessment of the human body movement pattern and positions via at least one of text, images, graphs, spreadsheets, 3D or multi-layered meshes, landmarks, avatar, or 3D pointclouds, heatmaps, videos, or virtual reality, and finite element analysis of particles.

In an embodiment, the human body or the part thereof is that of an individual person, and the output comprises an estimate of the individual person's: movements, motion, speed, acceleration, angles, joint angles, forces, joint forces, moments, joint moments kinetics, kinematics, or other analysis or assessment derived from one or more of these including physical, clinical, health and sport performance assessment, functional movement assessment or musculoskeletal assessment, clinical biomechanics assessment including pathological populations, injury prevention, motor development assessment including monitoring motor skill development in children or assessing people with Parkinson's disease, measurement of physical activity and automatically monitoring mentally ill patient or elders and other wellness and other relevant health and risk indicators.

According to another aspect there is a method for tracking, modelling, analysing and assessment of a human body movement or a specific human body part; the method comprising:

storing in a storage a dataset of diverse human data comprising one or more of imageries, videos, shapes, movements, motions, forces, moments, and relevant human health, physical, anatomical, clinical or biomechanical data of a full human body or a part thereof;

operating a controller and executing specific applications, and processes to process one or more of the human data and create a deformable, dynamic, scalable, digital twin module of the human body co-registered shape and composition and its movement patterns and movements limitations constrained by the human body anatomical, physical and biomechanical characteristics, to form a digital quantum model of a human and a quantum human graph;

creating the digital quantum human twin comprising;

(iv) using computer vison, statistical and machine learning models developed to facilitate slicing, matching and alignment of the human body shape, parts, data and images and its corresponding medical images, scans, particles, forces, moments, kinetic, kinematics and external environmental affecting factors, (v) storing the developed digital quantum human twin and;

(vi) capturing or receiving with an input one or more of the human movement data, human body photographs, frames, videos including audio, depth, static and dynamic shapes, or other sensory data or predicted human data by existing technologies;

digitizing the developed digital quantum human twin into particles in an optimized form able to facilitate its integration and application in desktops, smart devices and systems-on-chips, process the captured or received input together with the developed digital human twin and an offline dataset to facilitate accurate tracking, analyses and assessment of the human body movement or a specific human body part and generate an output;

the output can be real-time or non-real-times (or offline) and includes evaluation, analyses or assessment of one or more human movement patterns and any driven criteria, score, indicator, performance, forces, inertia, angles, stress, twist, speed, acceleration, orientation, momentum and risk of the body as a whole or in-parts; communicating the output;

wherein the data is pre-processed and inspected subjected to standardised clinical, physical, anatomical, biomedical and biomechanical constrained and limits relevant to the specific human body and its digital twin using advance statistical techniques and/or machine learning techniques and/or AI techniques to score each specific data type and its contribution in the analysis and movement of the human body or part thereof.

In an embodiment, the input can be marker or markerless data, information, formulas or features or a mathematical representation extracted from imageries, shapes or videos of the human body or a part thereof and the output can be the human body or part thereof, speed, acceleration, angles, joint angles, forces, joint forces, moments, joint moments kinetics, kinematics, or other analysis or assessment derived from one or more resource and include physical, clinical, health and sport performance assessment.

In an embodiment, the input can be invasive, non-invasive or external input or subjects or weight or forces or collision affecting the human body and its movement and contributing to the analysis and assessment of the human body, or a part thereof.

In an embodiment, the assessment and analysis processes comprises output performed by at least one computer vision (CV) approach, machine learning (ML), and/or artificial intelligence (AI) model.

In an embodiment, the movement of the human body being assessed belongs to a category or a group or a class of bodies and movement patterns, and the database comprises details of a plurality of different movements of the same or different human bodies belonging to the same, and/or a similar, category or group or class to that of the human body movement being analysed and assessed using the digital human twin.

In an embodiment, the human body and movement data and/or information comprises one or more of human motion or movement marker and markerless data, videos, photos, multiviews, full and/or partial body shapes or 3D surface scans, anthropometry, characteristics, attributes medical body composition imaging and health data, medical epidemiological and physiology information.

In an embodiment, there is provided a display for displaying a user interface, wherein the controller is operable and guided by electronic program instructions, to communicate the output by displaying the output via the display depicting a visualization of the analysis and assessment of the human body movement pattern and positions via at least one of text, images, graphs, spreadsheets, 3D or multi-layered meshes, avatar, or 3D pointclouds, heatmaps, videos, or virtual reality or finite element analysis of particles.

In an embodiment, the human body or the part thereof is that of an individual person, and the output comprises an estimate of the individual person's: movements, motion, speed, acceleration, angles, joint angles, forces, joint forces, moments, joint moments kinetics, kinematics, or other analysis or assessment derived from one or more of these including physical, clinical, health and sport performance assessment, functional movement assessment or musculoskeletal assessment, clinical biomechanics assessment including pathological populations, injury prevention, motor development assessment including monitoring motor skill development in children or assessing people with Parkinson's disease, measurement of physical activity and automatically monitoring mentally ill patient or elders and other wellness and other relevant health and risk indicators.

In an embodiment, there is a computer-readable storage medium on which is stored instructions that, when executed by a processor, causes the processor to perform a method described above.

In an embodiment, the at least one input representation of the human body and its movement is in the form of numbers and/or text and/or data and/or images and/or videos of any type or format.

According to an aspect there is a method of production of a digital twin of an individual person, comprising:

receiving a 3D representation of the individual person;

receiving medical images of the individual person;

forming a representation of the individual person from the 3D representation and the medical images as a model of a body shape and anatomical structure of the individual person;

segmenting the body shape and anatomical structure into slices and into positions in each slice;

allocating a composition type to each position in each slice.

In an embodiment, the model comprises bone structure, density scores, hierarchy, connectivity, joints, joint rotation and allowable movements.

According to an aspect there is a method of performing human movement analysis comprising:

receiving an input of a representation of an individual human;

fitting a skeleton to the representation;

using the skeleton to align a digital twin model of the individual human;

evaluating the human movement using anatomical structure of the digital twin model.

In an embodiment, the digital twin model is produced by:

receiving a 3D representation of the individual person;

receiving medical images of the individual person;

forming a representation of the individual person from the 3D representation and the medical images as a model of a body shape and anatomical structure of the individual person;

segmenting the body shape and anatomical structure into slices and into positions in each slice;

allocating a composition type to each position in each slice.

REFERENCES

[1] J. Durkin, and J. Dowling, Analysis of body segment parameter differences between four human populations and the estimation errors of four popular mathematical models. *Journal of Biomechanical Engineering,* 125 (4), 515-522, 2003.

[2] J. Xiaofei and L. Honghai Advances in View-Invariant Human Motion Analysis: A Review, IEEE Systems, Man, and Cybernetics, Vol. 40 (1), pp. 13-24, 2010.

[3] D. Roetenberg. Inertial and magnetic sensing of human motion. PhD thesis, 2006

[4] A. J. Callaway, et al. "A Comparison of Video and Accelerometer Based Approaches Applied to Performance Monitoring in Swimming", *Int. Journal of Sports Science & Coaching,* Vol. 4, No 1, pp. 139-153, 2009.

[5] T. Moeslund et al., "A survey of advances in vision-based human motion capture and analysis", *Computer Vision and Image Understanding,* vol. 104 (2), 2006.

[6] S. Corazza et. al., "Markerless Motion Capture through Visual Hull, Articulated ICP and Subject Specific Model Generation", *IJCV,* Volume 87, No 1-2, pp. 156-169, 2009.

[7] Amar A. El-Sallam et. al., "A low cost visual hull based markerless system for the optimization of athletic techniques in outdoor environments", *GRAPP,* 2013.

[8] Amar A. El-Sallam et. al., "A low cost 3D markerless system for the reconstruction of athletic techniques", *WACV,* 2013.

[9] M. Keys, Establishing computational fluid dynamic models for swimming technique assessment, PhD Thesis, U WA, 2010.

[10] D. Giansanti et. al., "Is it feasible to reconstruct body segment 3-D position and orientation using accelerometric data?", *IEEE Trans. Biomed. Eng* 50 (2003) 476-483.

[11] M. Rossi, A. El-Sallam et. al. "A Novel Approach to Calculate Body Segments Inertial Parameters from DXA and 3D Scanners" Data ", 4th International Conference on Computational Methods (ICCM2012), 2012.

[12] S. Foo, An Automatic Markerless Motion Analysis System for Tremor and Gait Assessment in Clinical Settings, honor thesis.

[13] Lee et al., Measurement of body segment parameters using dual energy X-ray absorptiometry and three-dimensional geometry: An application in gait analysis. *Journal of Biomechanics,* pp 217-222, 2009.

[14] S. Pellegrini et al., "A Generalization of the ICP Algorithm for Articulated Bodies", *BMVC,* 2008.

[15] Munawar Hayat, M. Bennamoun and Amar A. El-Sallam, "Clustering of video-patches on Grassmannian manifold for facial expression recognition from 3D videos", WACV 2013.

[16] D H. Parks & S. S. Fels, "Evaluation of Background Subtraction Algorithms with Post-processing", *Proc. IEEE* Fifth Inter. Conf. on Advanced Video and Signal Based Surveillance pp. 192-199, 2008.

[17] Y. Benezeth et. al, Review and evaluation of commonly-implemented background subtraction algorithms, *ICPR,* pp. 14, 2008.

[18] R. Radke et al. Image change detection algorithms: a systematic survey, *IEEE Trans on Image Processing,* 14 (3): 294307, 2005

[19] B. Tekin, A. Rozantsev, V. Lepetit and P. Fua, "Direct Prediction of 3D Body Poses from Motion Compensated Sequences," 2016 IEEE Conference on Computer Vision and Pattern Recognition (CVPR), 2016, pp. 991-1000, doi: 10.1109/CVPR.2016.113.

[20] J. Staynor, M. Smith, C. Donnelly, A. El-Sallam, T. Ackland, "DXA reference values and anthropometric screening for visceral obesity in Western Australian adults", Nature, October 2020.

[21] Alexander, C. F., Lum, I., Reid, S., Clarke, E., Stannage, K., A. El-Sallam, Herbert, R. D. & Donnelly, C. J., "A simple but reliable method for measuring 3D Achilles tendon moment arm geometry from a single, static magnetic resonance scan," 11 Apr. 2017 In: *Journal of Biomechanics.* 55, p. 134-138 5 p.

[22] Hayat, M., Bennamoun, M. & A. El-Sallam, "An RGB-D based image set classification for robust face recognition from Kinect data" 1 Jan. 2016 In: J. of Neurocomputing. 171, p. 889-900

[23] Rossi, M., Alderson, J., A. El-Sallam, Dowling, J., Reinbolt, J. & Donnelly, C. J., "A new validation technique for estimations of body segment inertia tensors: Principal axes of inertia do matter", 2016 In: *Journal of Biomechanics.* 49, 16, p. 4119-4123.

[24] S. Elaiwat, M. Bennamoun, F. Bousaid and A El-Sallam, "A Curvelet-based approach for textured 3D face recognition", Pattern Recognition, 2015.

[25] S. Elaiwat, M. Bennamoun, F. Bousaid and A El-Sallam, "3D Face Recognition Using Curvelet Local Features", IEEE Signal Processing Letter, 2014.

[26] El-Sallam Abd, A., & Mian, A. (2010). Human Body Pose Estimation from Still Images and Video Frames. In A. Campilho, & M. Kamel (Eds.), *Lecture Notes in Computer Science* (Vol. 1, pp. 176-188). Springer.

[27] Rossi, M. M., Donnelly, C. J., A. El-Sallam, Dowling, J., Reinbolt, J. A. & Alderson, J., "Validation of a DXA-based method for obtaining inertia tensors: "when pigs fly", 2016 ISBS *Conference Proceedings:* 34th International Conference on Biomechanics in Sports. Ae, M., Enomoto, Y., Fujii, N. & Takagi, H. (eds.). International Society of Biomechanics in Sports, p. 93-96

[28] A. El-Sallam, M. Bennamoun, K. Honda, A. Lyttle, J. Alderson, "Towards a fully automatic markerless motion analysis system for the estimation of body joint kinematics with application to sport analysis", International Joint Conference on Computer Vision, Imaging and Computer Graphics Theory and Applications, GRAPP, 2015.

[29] I-Zack Luml, Cyril Donnelly, Siobhan Reid, Caroline Davis, Catherine Elliott, Jane Valentine, A. El-S allam, "Achilles Tendon Moment Arm Geometry in Typically Developing Children", ISB2015 Congress, 2015.

[30] S. Afaq, M. Bennamoun, F. Boussaid A. El-Sallam "A Novel Local Surface Description for Automatic 3D Object Recognition in Low Resolution Cluttered Scenes", International Conference on Computer Vision (ICCV) workshop 2013.

[31] M. Rossi, N. Benjanuvatra, A. El-Sallam, A. Lyttle, and B. Blanksby, "Trunk Inertial Parameters Of Elite Male And Female Swimmers: Analysis Using Dxa And Estimation Of Errors From Indirect Estimation Methods", XXIV Congress of the International Society of Biomechanics (ISB2013), Brazil, 2013.

[32] A. Shah, M. Bennamoun, F. Boussaid, A. El-Sallam, "3D-Div: A novel local surface descriptor for feature matching and pairwise range image registration", ICIP 2013.

[33] S. Sedai, M. Bennamoun, D. Huynh A. El-Sallam, S. Foo, J. Alderson, C. Lind, "3D Human Pose Tracking using Gaussian Process regression and Particle Filter applied to gait analysis of Parkinson's", The 8th IEEE Conference on Industrial Electronics and Applications (ICIEA), (Accepted), 2013

[34] A. El-Sallam et. al., "A low cost 3D markerless system for the reconstruction of athletic techniques", IEEE Workshop on the Applications of Computer Vision, WACV, 2013.

[35] A. El-Sallam et. al., "A low cost visual hull based markerless system for the optimization of athletic techniques in outdoor environments", 8th International Joint Conference on Computer Vision, Imaging and Computer Graphics Theory and Applications, GRAPP 2013.

[36] Munawar Hayat, Mohammed Bennamoun, and A. El-Sallam, "Clustering of video-patches on Grassmannian manifold for facial expression recognition from 3D videos", IEEE Workshop on the Applications of Computer Vision, WACV, 2013.

[37] Said Elaiwat, Farid Boussaid, Mohammed Bennamoun, and A. El-Sallam, "3D Face Identification Using Curvelet Transform", ICCSPA'2013.

[38] S. A. Ali Shah, M. Bennamoun, F. Boussaid, and A. El-Sallam, "Automatic object detection using objectness measure", ICCSPA, 2013.

[39] Yinjie Lei, M. Bennamoun and A. El-Sallam, "A Structured Template based 3D Face Recognition Approach", IVCNZ. 2012.

[40] M. Rossi, A. El-Sallam, N. Benjanuvatra, A. Lyttle, and B. Blanksby, and M. Bennamoun, "A Novel Approach to Calculate Body Segments Inertial Parameters from DXA and 3D Scanners Data", 4th International Conference on Computational Methods (ICCM2012), 2012.

[41] Koji Honda, Matt Keys, Andrew Lyttle, Jacqueline Alderson, Mohammed Bennamoun, A El-Sallam, "Freestyle swimming an insight into propulsive and resistive mechanisms", 30 International Conference on Biomechanics in Sports, 2012.

[42] Munawar Hayat, M. Bennamoun and A. El-Sallam, "Fully Automatic Expression Invariant Facial Recognition from 3D Videos", International Conference on Pattern Recognition, ICPR, 2012.

[43] Munawar Hayat, M. Bennamoun and A. El-Sallam, "Evaluation of Spatiotemporal Detectors and Descriptors for Facial Expression Recognition", In Proc. of the 5th International Conference on Human System Interactions (HSI), 2012.

[44] A. El-Sallam, F. Sohel, and M. Bennamoun, "Robust Pose Invariant Shape-based Hand Recognition", IEEE ICIEA, 2011.

[45] A. El-Sallam, A. Mian, "A Novel Analytical Approach for Lip Synchronization", IEEE ICIP, pp. 2413-2416, 2010.

[46] Alderson et al., "Multi-source Databases, Machine Learning and Markerless Motion Capture: Why Applied Sports Biomechanics Needs Big Data", ISB Congress, Glasgow U.K., 2015, 2 pages.

The Claims Defining the Invention are as Follows:

1. A device for tracking, modelling, analysing and assessment of a human body movement or a specific human body part; the device comprising:
  a storage storing a dataset of diverse human data comprising one or more of imageries, videos, shapes, movements, motions, forces, moments, and relevant human health, physical, anatomical, clinical or biomechanical data of a full human body or a part thereof;
  a computing controller integrated with storage for storing electronic programs and instructions for operating the controller and executing specific applications and processes to process one or more of the human data and creating a deformable, dynamic, scalable, digital twin model of the human body co-registered shape and composition and its movement patterns and movements limitations constrained by the human body anatomical, physical and biomechanical characteristics, to form a digital quantum model of a human and a quantum human graph;
  the step of creating the deformable, dynamic, scalable, digital twin model of the human body comprising a computer integrated with;
  (i) computer vison, statistical and machine learning models developed to facilitate slicing, matching and alignment of the human body shape, parts, data and images and its corresponding medical images, scans, particles, forces, moments, kinetic, kinematics and external environmental affecting factors,
  (ii) a storage storing the developed digital quantum human twin and;
  (iii) input device operable to capture or receive one or more input data of the human movement data, human body photographs, frames, videos including audio, depth, static and dynamic shapes, or other sensory data or predicted human data;
  the developed digital quantum human twin is digitized into particles and is optimized in a form able to facilitate its integration and application in desktops, smart devices and systems-on-chips, process the captured or received input together with the developed digital human twin and an offline dataset to facilitate accurate tracking, analyses and assessment of the human body movement or a specific human body part and generate an output;
  the output can be real-time or non-real-times and includes evaluation, analyses or assessment of one or more human movement patterns and any driven criteria, score, indicator, performance, forces, inertia, angles, stress, twist, speed, acceleration, orientation, momentum and risk of the body as a whole or in-parts; communicate the output;
  wherein the data is pre-processed and inspected subjected to standardised clinical, physical, anatomical, biomedical and biomechanical constraints and limits relevant to the specific human body and its digital twin using advance statistical techniques and/or machine learning techniques and/or AI techniques to score each specific data type and its contribution in the analysis and movement of the human body or part thereof.

2. A device according to claim 1, wherein the input data comprises one or more of marker or markerless data, information, formulas or features or a mathematical representation extracted from imageries, shapes or videos of the human body or a part thereof and the output can be the human body or part thereof, speed, acceleration, angles, joint angles, forces, joint forces, moments, joint moments kinetics, kinematics, or other analysis or assessment derived from one or more resource and include physical, clinical, health and sport performance assessment.

3. A device according to claim 1, wherein the input data comprises one or more of invasive, non-invasive or other external input or subjects or weight or forces or collision affecting the human body and its movement and contributing to the analysis and assessment of the human body, or a part thereof.

4. A device according to claim 1, wherein the assessment and analysis processes comprises output performed by at least one computer vision (CV) approach, machine learning (ML), and/or artificial intelligence (AI) model.

5. A device according to claim 1, wherein the movement of the human body being assessed belongs to a category or a group or a class of bodies and movement patterns, and the database comprises details of a plurality of different movements of the same or different human bodies belonging to the same, and/or a similar, category or group or class to that of the human body movement being analysed and assessed using the digital human twin.

6. A device according to claim 5, wherein the human body and movement data and/or information comprises one or more of human motion or movement marker and markerless data, videos, photos, multiviews, full and/or partial body shapes or 3D surface scans, anthropometry, characteristics, attributes medical body composition imaging and health data, medical epidemiological and physiology information.

7. A device according to claim 1, comprising a display for displaying a user interface, wherein the controller is operable and guided by electronic program instructions, to communicate the output by displaying the output via the display depicting a visualization of the analysis and assessment of the human body movement pattern and positions via at least one of text, images, graphs, spreadsheets, 3D or multi-layered meshes, landmarks, avatar, or 3D pointclouds, heatmaps, videos, or virtual reality, and finite element analysis of particles.

8. A device according to claim 1, wherein the human body or the part thereof is that of an individual person, and the output comprises an estimate of the individual person's: movements, motion, speed, acceleration, angles, joint angles, forces, joint forces, moments, joint moments kinetics, kinematics, or other analysis or assessment derived from one or more of these including physical, clinical, health and sport performance assessment, functional movement assessment or musculoskeletal assessment, clinical biomechanics assessment including pathological populations, injury prevention, motor development assessment including monitoring motor skill development in children or assessing people with Parkinson's disease, measurement of physical activity and automatically monitoring mentally ill patient or elders and other wellness and other relevant health and risk indicators.

9. A method for tracking, modelling, analysing and assessment of a human body movement or a specific human body part; the method comprising:

a storage storing in a storage a dataset of diverse human data comprising one or more of imageries, videos, shapes, movements, motions, forces, moments, and relevant human health, physical, anatomical, clinical or biomechanical data of a full human body or a part thereof;

operating a controller and executing specific applications, and processes to process one or more of the human data and create a deformable, dynamic, scalable, digital twin module of the human body co-registered shape and composition and its movement patterns and movements limitations constrained by the human body anatomical, physical and biomechanical characteristics, to form a digital quantum model of a human and a quantum human graph;

creating the digital quantum human twin comprising;

(iv) using computer vison, statistical and machine learning models developed to facilitate slicing, matching and alignment of the human body shape, parts, data and images and its corresponding medical images, scans, particles, forces, moments, kinetic, kinematics and external environmental affecting factors, (v) storing the developed digital quantum human twin and;

(vi) capturing or receiving with an input one or more of the human movement data, human body photographs, frames, videos including audio, depth, static and dynamic shapes, or other sensory data or predicted human data by existing technologies;

digitizing the developed digital quantum human twin into particles in an optimized form able to facilitate its integration and application in desktops, smart devices and systems-on-chips, process the captured or received input together with the developed digital human twin and an offline dataset to facilitate accurate tracking, analyses and assessment of the human body movement or a specific human body part and generate an output;

the output can be real-time or non-real-times and includes evaluation, analyses or assessment of one or more human movement patterns and any driven criteria, score, indicator, performance, forces, inertia, angles, stress, twist, speed, acceleration, orientation, momentum and risk of the body as a whole or in-parts;

communicating the output;

wherein the data is pre-processed and inspected subjected to standardised clinical, physical, anatomical, biomedical and biomechanical constraints and limits relevant to the specific human body and its digital twin using advance statistical techniques and/or machine learning techniques and/or AI techniques to score each specific data type and its contribution in the analysis and movement of the human body or part thereof.

10. A method according to claim 9, wherein the input can be marker or markerless data, information, formulas or features or a mathematical representation extracted from imageries, shapes or videos of the human body or a part thereof and the output can be the human body or part thereof, speed, acceleration, angles, joint angles, forces, joint forces, moments, joint moments kinetics, kinematics, or other analysis or assessment derived from one or more resource and include physical, clinical, health and sport performance assessment.

11. A method according to claim 9, wherein the input can be invasive, non-invasive or external input or subjects or weight or forces or collision affecting the human body and its movement and contributing to the analysis and assessment of the human body, or a part thereof.

12. A method according to claim 9, wherein the assessment and analysis processes comprises output performed by at least one computer vision (CV) approach, machine learning (ML), and/or artificial intelligence (AI) model.

13. A method according to claim 9, wherein the movement of the human body being assessed belongs to a category or a group or a class of bodies and movement patterns, and the database comprises details of a plurality of different movements of the same or different human bodies belonging to the same, and/or a similar, category or group or class to that of the human body movement being analysed and assessed using the digital human twin.

14. A method according to claim 13, wherein the human body and movement data and/or information comprises one or more of human motion or movement marker and markerless data, videos, photos, multiviews, full and/or partial body shapes or 3D surface scans, anthropometry, characteristics, attributes medical body composition imaging and health data, medical epidemiological and physiology information.

15. A method according to claim 9, comprising a display for displaying a user interface, wherein the controller is operable and guided by electronic program instructions, to communicate the output by displaying the output via the display depicting a visualization of the analysis and assessment of the human body movement pattern and positions via at least one of text, images, graphs, spreadsheets, 3D or multi-layered meshes, avatar, or 3D pointclouds, heatmaps, videos, or virtual reality or finite element analysis of particles.

16. A method according to claim 9, wherein the human body or the part thereof is that of an individual person, and the output comprises an estimate of the individual person's: movements, motion, speed, acceleration, angles, joint angles, forces, joint forces, moments, joint moments kinetics, kinematics, or other analysis or assessment derived from one or more of these including physical, clinical, health and sport performance assessment, functional movement assessment or musculoskeletal assessment, clinical biomechanics assessment including pathological populations, injury prevention, motor development assessment including monitoring motor skill development in children or assessing people with Parkinson's disease, measurement of physical activity and automatically monitoring mentally ill patient or elders and other wellness and other relevant health and risk indicators.

17. A non-transitory computer-readable storage medium on which is stored instructions that, when executed by a processor, causes the processor to perform a method according to claim 9.

18. A system for analysing a body movement comprising a device according claim 1 wherein the at least one input representation of the human body and its movement is in the form of numbers and/or text and/or data and/or images and/or videos of any type or format.

19. A method of production of a digital twin of an individual person, comprising:
receiving a 3D representation of the individual person;
receiving medical images of the individual person;
forming a representation of the individual person from the 3D representation and the medical images as a model of a body shape and anatomical structure of the individual person;
segmenting the body shape and anatomical structure into slices and into positions in each slice;
allocating a composition type to each position in each slice.

20. The method according to claim 19, wherein the model comprises bone structure, density scores, hierarchy, connectivity, joints, joint rotation and allowable movements.

21. A method of performing human movement analysis comprising:
receiving an input of a representation of an individual human;
fitting a skeleton to the representation;
using the skeleton to align a digital twin model of the individual human;
evaluating the human movement using anatomical structure of the digital twin model.

22. The method according to claim 21, wherein the digital twin model is produced by:
receiving a 3D representation of the individual person;
receiving medical images of the individual person;
forming a representation of the individual person from the 3D representation and the medical images as a model of a body shape and anatomical structure of the individual person;
segmenting the body shape and anatomical structure into slices and into positions in each slice;
allocating a composition type to each position in each slice.

* * * * *